United States Patent
Zheng et al.

(10) Patent No.: US 12,023,188 B2
(45) Date of Patent: Jul. 2, 2024

(54) SYSTEMS AND METHODS FOR SIMULTANEOUS MULTI-SLICE IMAGING

(71) Applicant: SHANGHAI UNITED IMAGING HEALTHCARE CO., LTD., Shanghai (CN)

(72) Inventors: Yuan Zheng, Houston, TX (US); Jian Xu, Houston, TX (US); Qi Liu, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 376 days.

(21) Appl. No.: 17/305,056

(22) Filed: Jun. 30, 2021

(65) Prior Publication Data
US 2023/0000452 A1    Jan. 5, 2023

(51) Int. Cl.
*A61B 6/46*    (2024.01)
*A61B 6/00*    (2006.01)
*G01R 33/483*    (2006.01)
*G06F 18/214*    (2023.01)
*G06N 20/00*    (2019.01)

(52) U.S. Cl.
CPC .......... *A61B 6/469* (2013.01); *A61B 6/5241* (2013.01); *G01R 33/4835* (2013.01); *G06F 18/214* (2023.01); *G06N 20/00* (2019.01)

(58) Field of Classification Search
CPC .......... G01R 33/20–64; G01R 33/4835; A61B 6/469; A61B 6/5241; G06F 18/214; G06N 20/00
See application file for complete search history.

(56) References Cited

U.S. PATENT DOCUMENTS

| | | | |
|---|---|---|---|
| 7,375,523 B1 | 5/2008 | Hancu | |
| 9,414,766 B2 | 8/2016 | Jesmanowicz et al. | |
| 10,670,677 B2 | 6/2020 | Cloos et al. | |
| 2014/0088406 A1* | 3/2014 | Dharmakumar | A61B 8/488 600/509 |
| 2019/0219654 A1 | 7/2019 | Park et al. | |
| 2021/0090306 A1 | 3/2021 | Akcakaya et al. | |
| 2022/0130080 A1* | 4/2022 | Zeller | G06T 5/10 |
| 2022/0180482 A1* | 6/2022 | Wang | A61B 5/0033 |

OTHER PUBLICATIONS

Du et al, "Adaptive convolutional neural networks for k-space data interpolation in fast magnetic resonance imaging" (published at https://arxiv.org/abs/2006.01385, Jun. 2020).*
Barth, Markus et al., Simultaneous Multislice (SMS) Imaging Techniques, Magnetic Resonance in Medicine, 75(1):63-81, 2016.
Breuer, Felix A. et al., Controlled Aliasing in Parallel Imaging Results in Higher Acceleration (CAIPIRINHA) for Multi-Slice Imaging, Magnetic Resonance in Medicine, 53(3): 684-691, 2005.
(Continued)

*Primary Examiner* — Casey L Kretzer
(74) *Attorney, Agent, or Firm* — METIS IP LLC

(57) ABSTRACT

A method for SMS imaging may include obtaining target k-space data related to a region of interest (ROI) of an object. The method may also include generate, based on the target k-space data using a trained reconstruction model, a plurality of target images each of which corresponds to one of a plurality of target slices of the ROI at one of a plurality of target acquisition periods.

20 Claims, 13 Drawing Sheets

(56) References Cited

OTHER PUBLICATIONS

Ferrazzi, Giulio et al., Autocalibrated Multiband CAIPIRINHA with Through-time Encoding: Proof of Principle and Application to Cardiac Tissue Phase Mapping, Magnetic Resonance in Medicine, 81(2): 1016-1030, 2018.

Chang, Min Hyun et al., Deep Learning for Undersampled MRI Reconstruction, Physics in Medicine & Biology, 2018, 15 pages.

Cheng, Jing et al., Model Learning: Primal Dual Networks for Fast MR Imaging, Medical Image Computing and Computer Assisted Intervention, 2019, 8 pages.

Setsompop, Kawin et al., Blipped-Controlled Aliasing in Parallel Imaging for Simultaneous Multislice Echo Planar Imaging With Reduced g-Factor Penalty, Magnetic Resonance in Medicine, 67: 1210-1224, 2012.

Hammernik, Kerstin et al., Learning a Variational Network for Reconstruction of Accelerated MRI Date, Magnetic Resonance in Medicine, 79: 3055-3071, 2018.

* cited by examiner

600

```
┌─────────────────────────────────────────────────────────────┐
│ Causing an MRI device to apply one or more multiband        │
│ excitation radio frequency (RF) pulses to an ROI of an      │──610
│ object to simultaneously excite, for one or more times, a   │
│ plurality of target slices of the ROI                       │
└─────────────────────────────────────────────────────────────┘
                              │
                              ▼
┌─────────────────────────────────────────────────────────────┐
│ Causing the MRI device to apply phase modulation to at      │
│ least one of the excited target slices by applying, to each │
│ of the at least one of the excited target slices, a transmit│──620
│ phase that varies with a plurality of target acquisition    │
│ periods and/or a phase encoding direction                   │
└─────────────────────────────────────────────────────────────┘
                              │
                              ▼
┌─────────────────────────────────────────────────────────────┐
│ Acquiring target k-space data from the plurality of excited │──630
│ target slices of the ROI at the plurality of target         │
│ acquisition periods                                         │
└─────────────────────────────────────────────────────────────┘
                              │
                              ▼
┌─────────────────────────────────────────────────────────────┐
│ Generating, based on the target k-space data using a trained│
│ reconstruction model, a plurality of target unaliased images│──640
│ each of which corresponds to one of the plurality of target │
│ slices at one of the plurality of target acquisition periods│
│ the trained reconstruction model including a machine        │
│ learning model                                              │
└─────────────────────────────────────────────────────────────┘
```

FIG. 6A

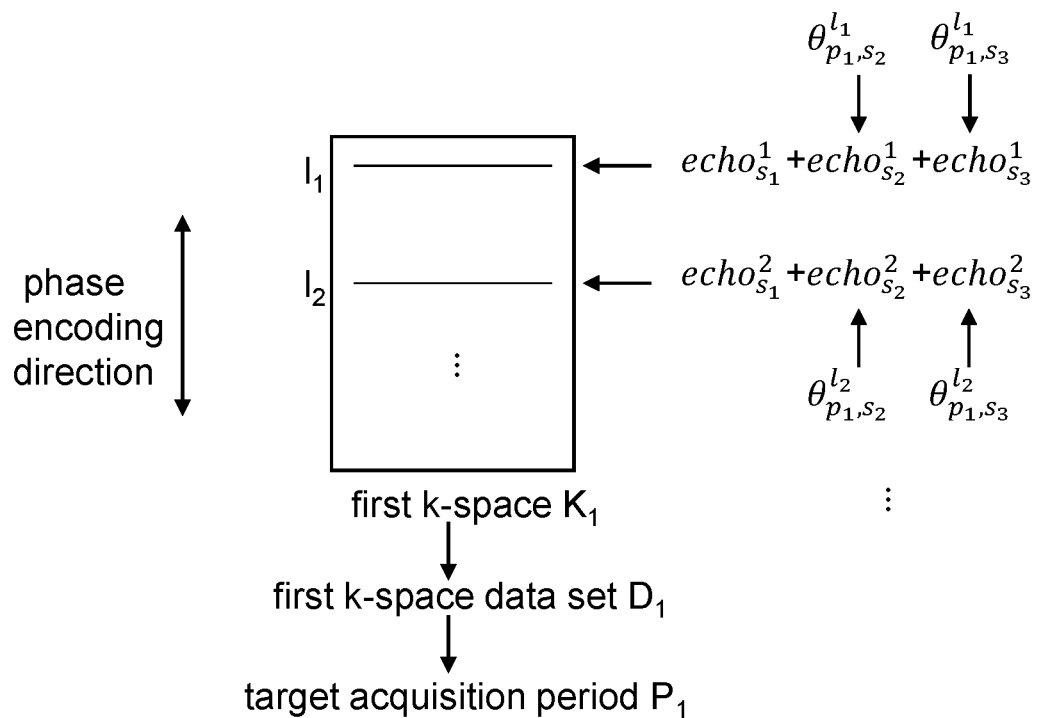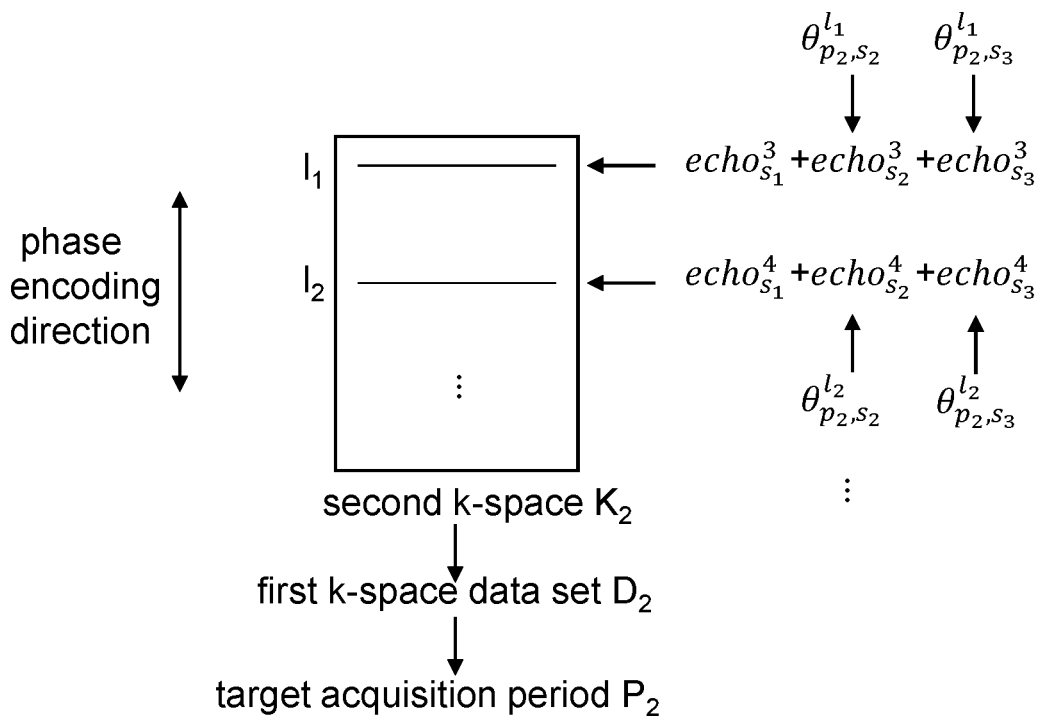
FIG. 6B

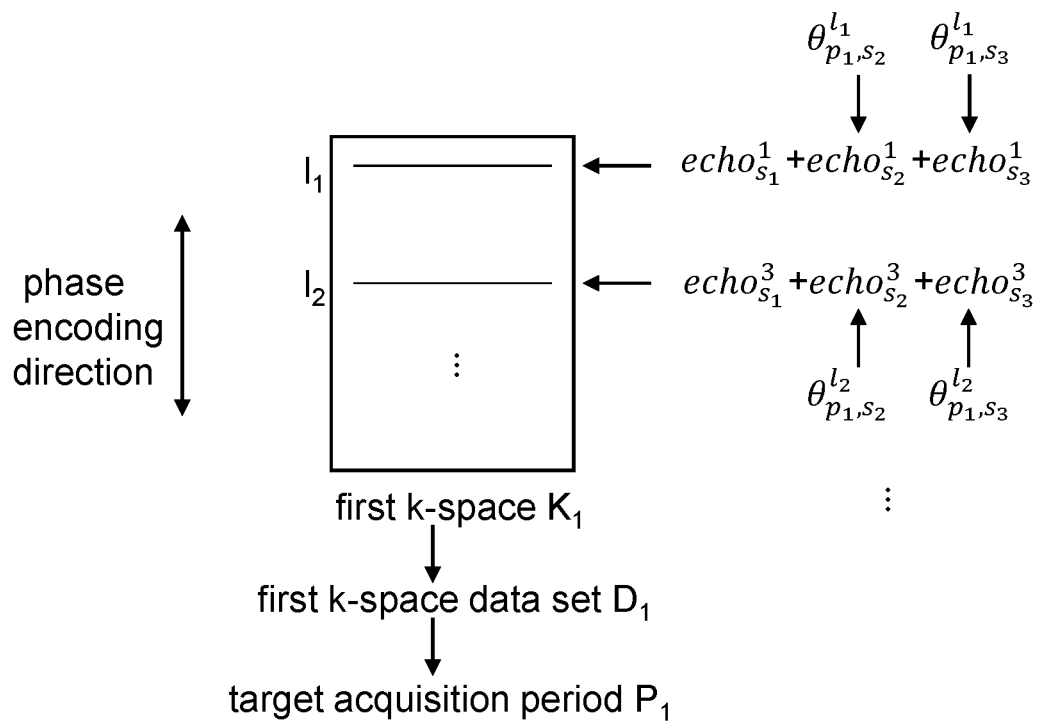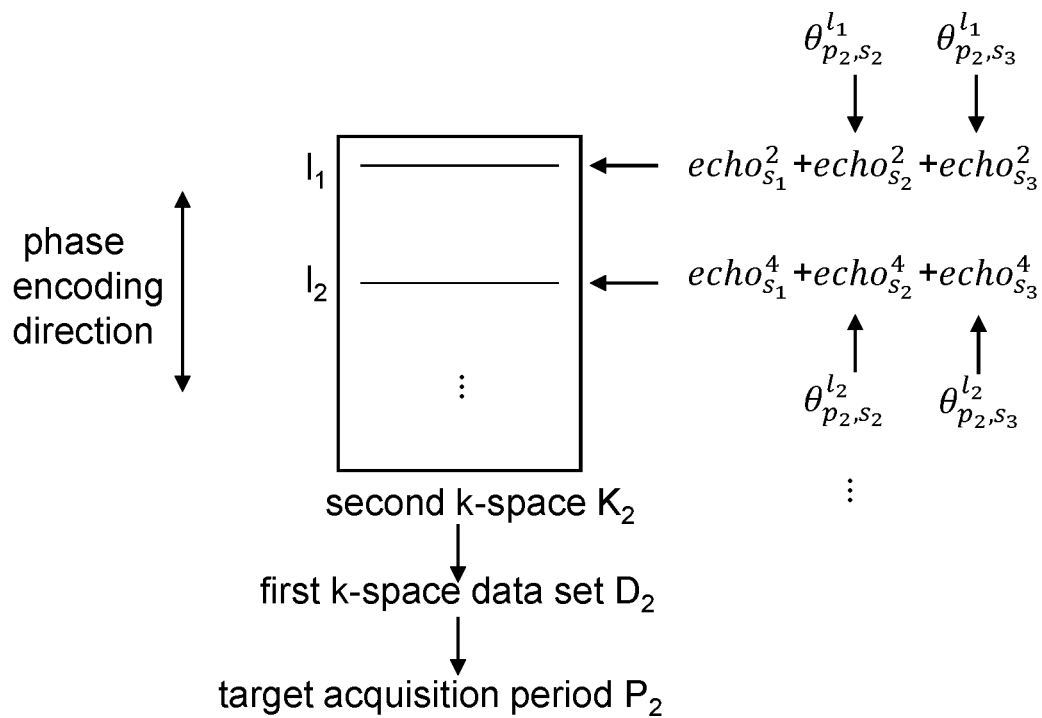
FIG. 6C

700

┌─────────────────────────────────────────────┐
│ Obtaining a plurality of training data sets, each of │ ~710
│ the plurality of training data sets including sample k- │
│ space data and a plurality of sample images │
└─────────────────────────────────────────────┘
                      ↓
┌─────────────────────────────────────────────┐
│ Obtaining the trained reconstruction model by │ ~720
│ training a preliminary model based on the plurality │
│ of training data sets │
└─────────────────────────────────────────────┘

FIG. 7

SYSTEMS AND METHODS FOR SIMULTANEOUS MULTI-SLICE IMAGING

TECHNICAL FIELD

The present disclosure generally relates to magnetic resonance imaging (MRI), and in particular, to systems and methods for simultaneous multi-slice (SMS) imaging.

BACKGROUND

Simultaneous multi-slice (SMS) imaging has rapidly advanced to become a major imaging technique for acceleration of magnetic resonance imaging (MRI). Compared with the imaging that only excites a single slice one time, SMS excites multiple slices at the same time and simultaneously acquires magnetic resonance (MR) signals generated from the multiple excited slices. The MR signals are filled into the k-space to generate k-space data. Because the received MR signals include the contributions of the multiple excited slices, reconstruction of the k-space data directly using inverse Fourier transform may lead to an aliased image of the multiple slices. Therefore, it is desirable to provide systems and/or methods for SMS reconstruction to generate an unaliased image for each slice.

SUMMARY

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

According to a first aspect of the present disclosure, a system for simultaneous multi-slice (SMS) imaging may include a magnetic resonance imaging (MRI) device configured to scan a region of interest (ROI) of an object, one or more storage devices, and one or more processors configured to communicate with the one or more storage devices. The one or more storage devices may include a set of instructions. When the one or more processors executing the set of instructions, the one or more processors may be directed to perform one or more of the following operations. The one or more processors may obtain target k-space data related to the ROI of the object. The one or more processors may generate, based on the target k-space data using a trained reconstruction model, a plurality of target images each of which corresponds to one of a plurality of target slices of the ROI at one of a plurality of target acquisition periods.

In some embodiments, the target k-space data may include a plurality of first k-space data sets each of which is acquired from the plurality of target slices in one of the plurality of target acquisition periods.

In some embodiments, the target k-space data may be undersampled.

In some embodiments, to generate, based on the target k-space data using the trained reconstruction model, the plurality of target images, the one or more processors may input the target k-space data into the trained reconstruction model. The one or more processors may output, by the trained reconstruction model, the plurality of target images based on the target k-space data.

In some embodiments, to obtain the target k-space data related to the ROI of the object, the one or more processors may cause the MRI device to apply one or more multiband excitation radio frequency (RF) pulses to the ROI to simultaneously excite, for one or more times, the plurality of target slices of the ROI. The one or more processors may cause the MRI device to apply phase modulation to at least one of the excited target slices by applying, to each of the at least one of the excited target slices, a transmit phase that varies with a plurality of target acquisition periods and/or a phase encoding direction. The one or more processors may acquire the target k-space data from the plurality of excited target slices of the ROI at the plurality of target acquisition periods.

In some embodiments, the transmit phases applied to two or more of the plurality of target slices may be different.

In some embodiments, to generate, based on the target k-space data using the trained reconstruction model, the plurality of target images, the one or more processors may generate a plurality of target aliased images by performing inverse Fourier transform on the target k-space data, each of the plurality of target aliased images corresponding to the plurality of target slices and one of the plurality of target acquisition periods. The one or more processors may input the plurality of aliased images into the trained reconstruction model. The one or more processors may output, by the trained reconstruction model, the plurality of target images based on the plurality of target aliased images.

In some embodiments, to generate, based on the target k-space data using the trained reconstruction model, the plurality of target images, the one or more processors may determine a plurality of reference data sets based on the target k-space data. Each of the plurality of reference data sets may correspond to one of the plurality of target slices and one of the plurality of target acquisition periods. The plurality of reference data sets may provide unaliased information for unaliasing of the plurality of target slices in the target k-space data. The one or more processors may generate, based on the target k-space data and the plurality of reference data sets, the plurality of target images using the trained reconstruction model.

In some embodiments, the trained reconstruction model may include a machine learning model.

In some embodiments, the trained reconstruction model may be provided by: obtaining a plurality of training data sets; and obtaining the trained reconstruction model by training a preliminary model based on the plurality of training data sets. Each of the plurality of training data sets may include sample k-space data and a plurality of sample unaliased images. Each of the plurality of sample unaliased images may correspond to one of a plurality of sample slices of a sample and one of a plurality of sample acquisition periods. For each of at least one of the plurality of sample slices, phases of the corresponding sample k-space data may vary based on the plurality of sample acquisition periods and/or the phase encoding direction.

In some embodiments, the sample k-space data may include real k-space data that is acquired by simultaneously exciting the plurality of sample slices. The plurality of sample unaliased images may be generated based on the sample k-space data.

In some embodiments, the sample k-space data may be undersampled.

In some embodiments, the sample k-space data may include synthesized k-space data. The synthesized k-space data may be obtained by obtaining a plurality of sample k-space data sets by performing Fourier transform on the plurality of sample unaliased images. Each of the plurality of sample k-space data sets may correspond to one of the plurality of sample unaliased images. The synthesized k-space data may be obtained further by applying phase modulation to the sample k-space data sets so that for each of at least one of the plurality of sample slices, the sample phases of the corresponding sample k-space data sets vary based on the plurality of sample acquisition periods and/or the phase encoding direction. The synthesized k-space data may be obtained further by obtaining a plurality of second k-space data sets by combining the sample k-space data sets corresponding to the sample acquisition period. Each of the plurality of second k-space data sets may correspond to the plurality of sample slices and one of the plurality of sample acquisition periods. The sample k-space data sets may include the plurality of second k-space data sets.

In some embodiments, the synthesized k-space data may be obtained further by applying an undersampling strategy to the plurality of second k-space data sets or the plurality of sample k-space data sets by replacing a portion of data in the plurality of second k-space data sets or the plurality of sample k-space data sets with zero.

In some embodiments, obtaining the trained reconstruction model by training the preliminary model based on the plurality of training data sets may include: for each of at least one of the plurality of training data sets, generating a plurality of sample aliased images by performing inverse Fourier transform on the sample k-space data of the training data set, each of the plurality of sample aliased images corresponding to the plurality of sample slices and one of the plurality of sample acquisition periods; and obtaining the trained reconstruction model by training the preliminary model based on the plurality of sample aliased images of the each of the at least one of the plurality of training data sets.

In some embodiments, obtaining the trained reconstruction model by training the preliminary model based on the plurality of training data sets may include obtaining the trained reconstruction model by performing an iteration process including one or more iterations. At least one of the one or more iterations may include outputting, by an intermediate model, a plurality of output images based on the sample k-space data of one of the plurality of training data sets. The intermediate model may include the preliminary model in a first iteration of the one or more iterations of the iteration process or an updated model generated in a previous iteration of the at least one of the one or more iterations. Each of the plurality of output images may correspond to one of the plurality of sample unaliased images of the one of the plurality of training data sets. The at least one of the one or more iterations may further include updating the intermediate model based on a difference between the plurality of output images and the plurality of sample unaliased images of the one of the plurality of training data sets.

In some embodiments, each of the plurality of target acquisition periods may correspond to a physiological motion phase of the ROI. The plurality of target images may form a physiological motion cine of the ROI.

In some embodiments, the ROI of the object may include at least a portion of a heart or a lung.

In some embodiments, the plurality of target images may be used for perfusion analysis and indicate a change of a density of a contrast agent in the plurality of target slices over time.

According to another aspect of the present disclosure, a method for SMS imaging may include one or more of the following operations. One or more processors may obtain target k-space data related to an ROI of an object. The one or more processors may generate, based on the target k-space data using a trained reconstruction model, a plurality of target images each of which corresponds to one of a plurality of target slices of the ROI at one of a plurality of target acquisition periods.

According to yet another aspect of the present disclosure, a system for SMS imaging may include an acquisition module configured to obtain target k-space data related to a region of interest (ROI) of an object. The system may also include a reconstruction module configured to generate, based on the target k-space data using a trained reconstruction model, a plurality of target images each of which corresponds to one of a plurality of target slices of the ROI at one of a plurality of target acquisition periods.

According to yet another aspect of the present disclosure, a non-transitory computer readable medium may comprise at least one set of instructions. The at least one set of instructions may be executed by one or more processors of a computing device. The one or more processors may obtain target k-space data related to an ROI of an object. The one or more processors may generate, based on the target k-space data using a trained reconstruction model, a plurality of target images each of which corresponds to one of a plurality of target slices of the ROI at one of a plurality of target acquisition periods.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 6A is a flowchart illustrating an exemplary process for SMS imaging according to some embodiments of the present disclosure;

FIGS. 6B and 6C are schematic diagrams illustrating exemplary acquisition of target k-space data according to some embodiments of the present disclosure;

FIG. 7 is a flowchart illustrating an exemplary process for obtaining a trained reconstruction model according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different levels in ascending order. However, the terms may be displaced by another expression if they achieve the same purpose.

Figure 3:
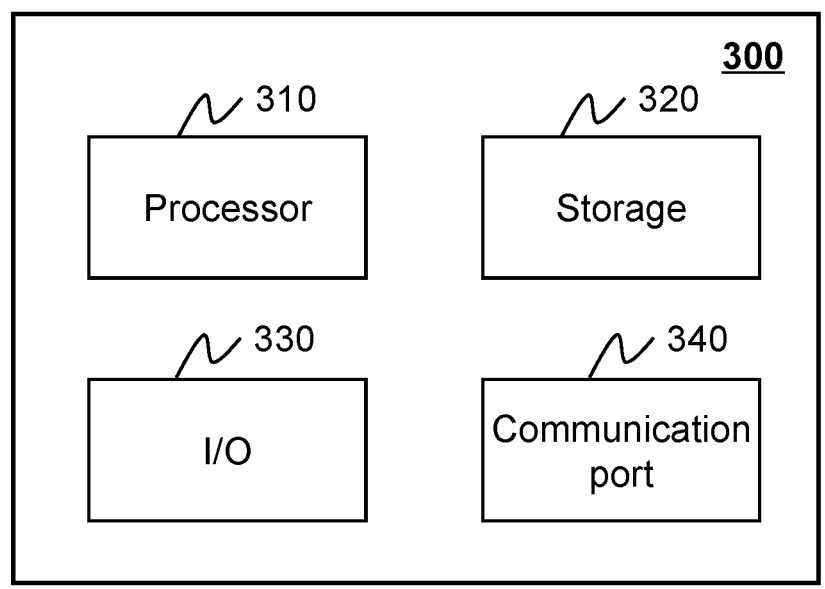
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical imaging and/or medical treatment. In some embodiments, the medical system may include an imaging system. The imaging system may include a single modality imaging system and/or a multi-modality imaging system. The single modality imaging system may include, for example, a magnetic resonance imaging (MRI) system. Exemplary MRI systems may include a superconducting magnetic resonance imaging system, a non-superconducting magnetic resonance imaging system, etc. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, etc. In some embodiments, the medical system may include a treatment system. The treatment system may include a treatment plan system (TPS), image-guided radiotherapy (IGRT) system, etc. The image-guided radiotherapy (IGRT) system may include a treatment device and an imaging device. The treatment device may include a linear accelerator, a cyclotron, a synchrotron, etc., configured to perform a radiotherapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc.

An aspect of the present disclosure relates to systems and methods for SMS imaging, and in particular, related to systems and methods for reconstruction of autocalibration acquisition data using a machine learning model. The autocalibration acquisition data may include the following features. The autocalibration acquisition data may be acquired from a plurality of slices of a region of interest (ROI) of an object that are simultaneously excited. The autocalibration acquisition data may be acquired in a plurality of acquisition periods so that a series of unaliased images each of which corresponds to one of the plurality of slices and one of the plurality of acquisition periods are reconstructed from the autocalibration acquisition data. The autocalibration acquisition data may be phase-modulated by applying a transmit phase that varies along the phase encoding direction and/or the temporal dimension (e.g., the plurality of acquisition periods). The reconstruction for the autocalibration acquisition data using a machine learning model is a non-linear approach, which may improve image quality and reconstruction speed.

A plurality of reference data sets that provide unaliased information for unaliasing of the plurality of slices may be determined based on the autocalibration acquisition data (k-space data), which indicates that the autocalibration acquisition data includes the unaliased information. Therefore, after the autocalibration acquisition data is input into the machine learning model, the machine learning model may automatically extract the unaliased information implied in the autocalibration acquisition data and output unaliased images. In this way, additional operations for obtaining the reference data sets (e.g., additional determination or scan for the reference data sets) are not required in SMS reconstruction, which improves the efficiency for SMS reconstruction.

Figure 1:
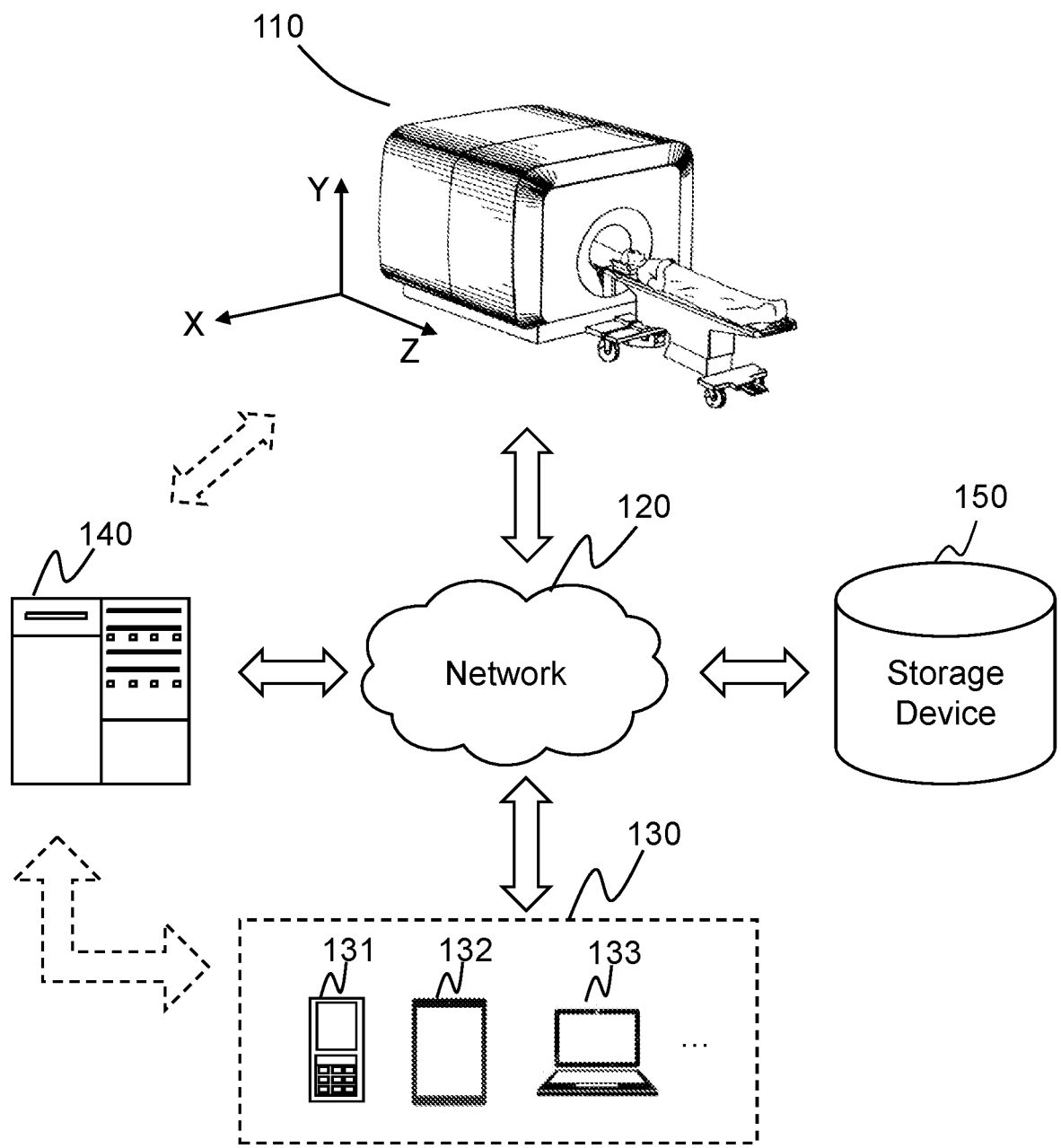
FIG. 1 is a schematic diagram illustrating an exemplary MRI system according to some embodiments of the present disclosure.

FIG. 1 is a schematic diagram illustrating an exemplary MRI system 100 according to some embodiments of the present disclosure. As illustrated, the MRI system 100 may include a scanner 110, a network 120, a user device 130, a processing device 140, and a storage device 150. The components of the MRI system 100 may be connected in one or more of various ways. Mere by way of example, as illustrated in FIG. 1, the scanner 110 may be connected to the processing device 140 through the network 120. As another example, the scanner 110 may be connected to the processing device 140 directly (as indicated by the bi-directional arrow in dotted lines linking the scanner 110 and the processing device 140). As a further example, the storage device 150 may be connected to the processing device 140 directly or through the network 120. As still a further example, the user device 130 (e.g., 131, 132, 133, etc.) may be connected to the processing device 140 directly (as indicated by the bi-directional arrow in dotted lines linking the user device 130 and the processing device 140) or through the network 120.

The scanner 110 may scan an object located within its detection region and generate a plurality of imaging data relating to the object. In the present disclosure, "subject" and "object" are used interchangeably. Mere by way of example, the object may include a patient, a man-made object, etc. As another example, the object may include a specific portion, organ, and/or tissue of a patient. For example, the object may include head, brain, neck, body, shoulder, arm, thorax, cardiac, stomach, blood vessel, soft tissue, knee, feet, or the like, or any combination thereof.

In some embodiments, the scanner 110 may include an MRI scanner, a multi-modality device, etc. Exemplary multi-modality device may include an MRI-CT device, a PET-MRI device, etc. In some embodiments, the MRI scanner may be a close-bore scanner or an open-bore scanner. In the present disclosure, the X axis, the Y axis, and the Z axis shown in FIG. 1 may form an orthogonal coordinate system. The X axis and the Z axis shown in FIG. 1 may be horizontal, and the Y axis may be vertical. As illustrated, the positive X direction along the X axis may be from the right side to the left side of the scanner 110 seen from the direction facing the front of the scanner 110; the positive Y direction along the Y axis shown in FIG. 1 may be from the lower part to the upper part of the scanner 110; the positive Z direction along the Z axis shown in FIG. 1 may refer to a direction in which the object is moved out of the scanning channel (or referred to as the bore) of the scanner 110. More description of the scanner 110 may be found elsewhere in the present disclosure. See, e.g., FIG. 2 and the description thereof.

The network 120 may include any suitable network that can facilitate the exchange of information and/or data for the MRI system 100. In some embodiments, one or more components of the MRI system 100 (e.g., the scanner 110, the user device 130, the processing device 140, or the storage device 150) may communicate information and/or data with one or more other components of the MRI system 100 via the network 120. For example, the processing device 140 may obtain magnetic resonance (MR) data (also referred to as MR signals, echo signals, or echo data) from the scanner 110 via the network 120. As another example, the user device 130 and/or the storage device 150 may obtain one or more images from the processing device 140. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the MRI system 100 may be connected to the network 120 to exchange data and/or information.

The user device 130 may include a mobile device 131, a tablet computer 132, a laptop computer 133, a desktop computer (not shown), a workstation (not shown), or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google™ Glass, an Oculus Rift, a Hololens, a Gear VR, etc. In some embodiments, the user device 130 may remotely operate the scanner 110 and/or the processing device 140. In some embodiments, the user device 130 may operate the scanner 110 and/or the processing device 140 via a wireless connection. In some embodiments, the user device 130 may receive information and/or instructions inputted by a user, and send the received information and/or instructions to the scanner 110 or to the processing device 140 via the network 120. For example, a user (e.g., a doctor, a technician, or an engineer, etc.) of the MRI system 100 may set a scan protocol though the user device 130. The user device 130 may send the scan protocol to the processing device 140 to direct the processing device 140 to cause the scanner 110 (e.g., the MRI scanner) to operate according to the scan protocol. In some embodiments, the user device 130 may receive data and/or information from the processing device 140 and/or the storage device 150. For example, the user device 130 may obtain one or more images from the processing device 140 and/or the storage device 150.

The processing device 140 may process data and/or information obtained from the scanner 110, the user device 130, and/or the storage device 150. For example, the processing device 140 may obtain MR data from the scanner 110 and determine one or more images based on the MR data. As another example, the processing device 140 may receive one or more instructions from the user device 130 and cause the scanner 110 to operate according to the one or more instructions. In some embodiments, the processing device 140 may be a single server, or a server group. The server group may be centralized or distributed. In some embodiments, the processing device 140 may be local or remote. For example, the processing device 140 may access information and/or data stored in or acquired by the scanner 110, the user device 130, and/or the storage device 150 via the network 120. As another example, the processing device 140 may be directly connected to the scanner 110 (as illustrated by the bidirectional arrow in dashed lines connecting the processing device 140 and the scanner 110 in FIG. 1), the user device 130 (as illustrated by the bidirectional arrow in dashed lines connecting the processing device 140 and the user device 130 in FIG. 1), and/or the storage device 150 to access stored or acquired information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 300 having one or more components illustrated in FIG. 3 in the present disclosure.

The storage device 150 may store data and/or instructions. In some embodiments, the storage device 150 may include a database, a picture archiving and communication system, a file system, or the like, or any combination thereof. In some embodiments, the storage device 150 may store data obtained from the scanner 110, the user device 130 and/or the processing device 140. For example, the storage device 150 may store MR data acquired by the scanner 110. As another example, the storage device 150 may store medical images (e.g., MRI images) generated by the processing device 140 and/or the user device 130. As a further example, the storage device 150 may store preset scan parameters (e.g., preset scan protocols) of the MRI system 100. In some embodiments, the storage device 150 may store data and/or instructions that the processing device 140 may execute or use to perform exemplary methods described in the present disclosure. For example, the storage device 150 may store instructions that the processing device 140 may execute to cause the scanner 110 to acquire MR data based on a pulse sequence including a steady-state sequence and an acquisition sequence. As another example, the storage device 150 may store instructions that the processing device 140 and/or the user device 130 may execute to generate one or more images based on the MR data. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the MRI system 100 (e.g., the scanner 110, the processing device 140, the user device 130, etc.). One or more components of the MRI system 100 may access the data or instructions stored in the storage device 150 via the network 120. In some embodiments, the storage device 150 may be directly connected to or communicate with one or more components of the MRI system 100 (e.g., the scanner 110, the processing device 140, the user device 130, etc.). In some embodiments, the storage device 150 may be part of the processing device 140.

In some embodiments, the MRI system 100 may further include one or more power supplies (not shown in FIG. 1) connected to one or more components of the MRI system 100 (e.g., the scanner 110, the processing device 140, the user device 130, the storage device 150, etc.).

Figure 2:
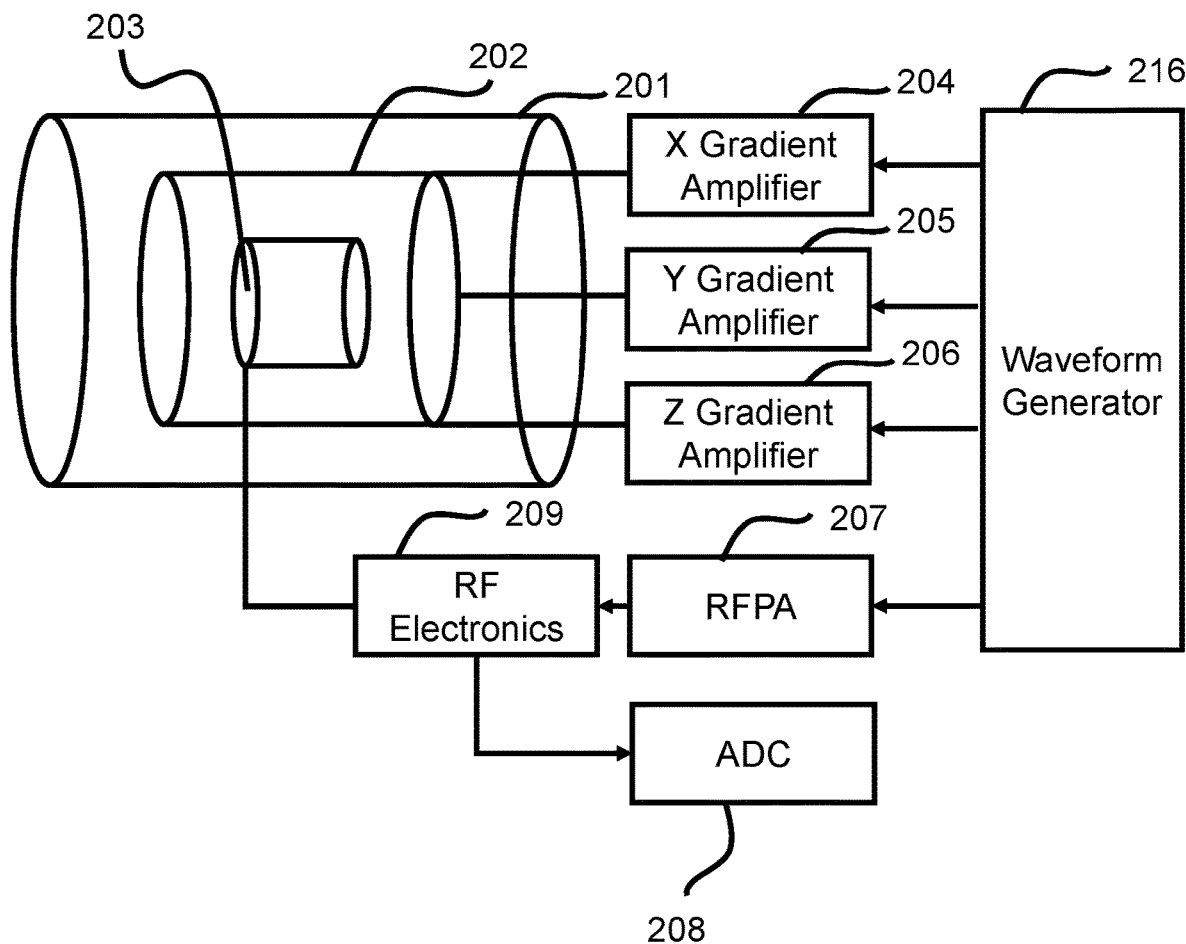
FIG. 2 is a schematic diagram illustrating an exemplary MRI scanner according to some embodiments of the present disclosure.

FIG. 2 is a schematic diagram illustrating an exemplary MRI scanner according to some embodiments of the present disclosure. As illustrated, the main magnet 201 may generate a first magnetic field (or referred to as a main magnetic field) that may be applied to an object (also referred to as a subject) exposed inside the field. The main magnet 201 may include a resistive magnet or a superconductive magnet that both need a power supply (not shown) for operation. Alternatively, the main magnet 201 may include a permanent magnet. The main magnet 201 may include a bore that the object is placed within. The main magnet 201 may also control the homogeneity of the generated main magnetic field. Some shim coils may be in the main magnet 201. The shim coils placed in the gap of the main magnet 201 may compensate for the inhomogeneity of the magnetic field of the main magnet 201. The shim coils may be energized by a shim power supply.

Gradient coils 202 may be located inside the main magnet 201. The gradient coils 202 may generate a second magnetic field (or referred to as a gradient field, including gradient fields Gx, Gy, and Gz). The second magnetic field may be superimposed on the main field generated by the main magnet 201 and distort the main field so that the magnetic orientations of the protons of an object may vary as a function of their positions inside the gradient field, thereby encoding spatial information into MR signals generated by the object being imaged. The gradient coils 202 may include X coils (e.g., configured to generate the gradient field Gx corresponding to the X direction), Y coils (e.g., configured to generate the gradient field Gy corresponding to the Y direction), and/or Z coils (e.g., configured to generate the gradient field Gz corresponding to the Z direction) (not shown in FIG. 2). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 202 may allow spatial encoding of MR signals for image reconstruction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the X axis, the Y axis, or the Z axis, respectively. The gradient coils 202 may be designed for either a close-bore MRI scanner or an open-bore MRI scanner. In some instances, all three sets of coils of the gradient coils 202 may be energized and three gradient fields may be generated thereby. In some embodiments of the present disclosure, the X coils and Y coils may be energized to generate the gradient fields in the X direction and the Y direction. As used herein, the X axis, the Y axis, the Z axis, the X direction, the Y direction, and the Z direction in the description of FIG. 2 are the same as or similar to those described in FIG. 1.

In some embodiments, radio frequency (RF) coils 203 may be located inside the main magnet 201 and serve as transmitters, receivers, or both. The RF coils 203 may be in connection with RF electronics 209 that may be configured or used as one or more integrated circuits (ICs) functioning as a waveform transmitter and/or a waveform receiver. The RF electronics 209 may be connected to a radiofrequency power amplifier (RFPA) 207 and an analog-to-digital converter (ADC) 208.

When used as transmitters, the RF coils 203 may generate RF signals that provide a third magnetic field that is utilized to generate MR signals related to the object being imaged. The third magnetic field may be perpendicular to the main magnetic field. The waveform generator 216 may generate an RF pulse. The RF pulse may be amplified by the RFPA 207, processed by the RF electronics 209, and applied to the RF coils 203 to generate the RF signals in response to a powerful current generated by the RF electronics 209 based on the amplified RF pulse.

When used as receivers, the RF coils may be responsible for detecting MR signals (e.g., echoes). After excitation, the MR signals generated by the object may be sensed by the RF coils 203. The receive amplifier then may receive the sensed MR signals from the RF coils 203, amplify the sensed MR signals, and provide the amplified MR signals to the ADC 208. The ADC 208 may transform the MR signals from analog signals to digital signals. The digital MR signals then may be filled into k-space.

In some embodiments, the gradient coils 202 and the RF coils 203 may be circumferentially positioned with respect to the object. It is understood by those skilled in the art that the main magnet 201, the gradient coils 202, and the RF coils 203 may be situated in a variety of configurations around the object.

In some embodiments, the RFPA 207 may amplify an RF pulse (e.g., the power of the RF pulse, the voltage of the RF pulse) such that an amplified RF pulse is generated to drive the RF coils 203. In some embodiments, the RFPA 207 may include one or more RFPAs.

In some embodiments, the scanner 110 may further include an object positioning system (not shown). The object positioning system may include an object cradle and a transport device. The object may be placed on the object cradle and be positioned by the transport device within the bore of the main magnet 201.

MRI systems (e.g., the MRI system 100 in the present disclosure) may be commonly used to obtain an interior image from an object (e.g., a patient) for a particular region of interest that can be used for the purposes of, e.g., diagnosis, treatment, or the like, or a combination thereof. MRI systems include a main magnet (e.g., the main magnet 201) assembly for providing a main magnetic field to align the individual magnetic moments of the H atoms within the patient's body. During this process, the H atoms oscillate around their magnetic poles at their characteristic Larmor frequency. If the object is subjected to an additional magnetic field, which is tuned to the Larmor frequency, the H atoms absorb additional energy, which rotates the net aligned moment of the H atoms. The additional magnetic field may be provided by an RF excitation signal (e.g., the RF signal generated by the RF coils 203). When the additional magnetic field is removed, the magnetic moments of the H atoms rotate back into alignment with the main magnetic field, thereby emitting an MR signal. The acquired MR signals may be digitized and filled into the k-space. One or more images may be generated based on the k-space data. In the present disclosure, terms "MR data," "MR signal," "echo," "echo data," and "echo signal" may be used interchangeably.

If the main magnetic field is uniform across the entire body of the patient, then the RF excitation signal may excite all of the H atoms in the sample non-selectively. Accordingly, in order to image a particular portion of the patient's body, magnetic field gradients Gx, Gy, and Gz (e.g., generated by the gradient coils 202) in the X, Y, and Z directions (e.g., same as or similar to the X axis, the Y axis, and the Z axis in FIG. 1), having a particular timing, frequency, and phase, may be superimposed on the magnetic field such that the RF excitation signal excites the H atoms in one or more target slices of the patient's body, and unique phase and frequency information is encoded in the MR signal depending on the location of the H atoms in the "image slice."

FIG. 3 is a schematic diagram illustrating exemplary hardware and/or software components of a computing device on which the processing device 140 may be implemented according to some embodiments of the present disclosure. As illustrated in FIG. 3, the computing device 300 may include a processor 310, a storage 320, an input/output (I/O) 330, and a communication port 340.

The processor 310 may execute computer instructions (program code) and perform functions of the processing device 140 in accordance with techniques described herein. The computer instructions may include routines, programs, objects, components, signals, data structures, procedures, modules, and functions, which perform particular functions described herein. For example, the processor 310 may generate one or more images based on MR data. In some embodiments, the processor 310 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 300. However, it should be noted that the computing device 300 in the present disclosure may also include multiple processors, and thus operations of a method that are performed by one processor as described in the present disclosure may also be jointly or separately performed by the multiple processors. For example, if in the present disclosure the processor of the computing device 300 executes both operations A and B, it should be understood that operations A and B may also be performed by two different processors jointly or separately in the computing device 300 (e.g., a first processor executes operation A and a second processor executes operation B, or the first and second processors jointly execute operations A and B).

Merely by way example, the processor 310 may receive instructions to follow an MRI scan protocol for imaging/scanning the object. For example, the processor 310 may instruct the object positioning system of the scanner 110 to move the object to a proper position within the bore of the main magnet 201. As another example, the processor 310 may also provide certain control signals to control the main magnet 201 to generate a main magnet field with a specific strength.

The processor 310 may receive control signals to set the shape, amplitude, and/or timing of the gradient waveforms and/or the RF waveforms, and send the set parameters to the waveform generator 216 to instruct the waveform generator 216 to generate a particular gradient waveform sequence and pulse sequence that are to be applied to the gradient coils 202 and the RF coils 203 through the amplifiers 204-207, respectively.

The processor 310 may also sample data (e.g., echoes) from the RF coils 203 based on one or more sampling parameters including, e.g., timing information (e.g., the length of data acquisition), the type of k-space data acquisition (e.g., undersampling, oversampling, etc.), sampling trajectory (e.g., a Cartesian trajectory, a non-Cartesian trajectory such as spiral trajectory, radial trajectory, etc.), or the like, or a combination thereof. In some embodiments, the timing information may be input by a user (e.g., an operator) or autonomously determined by the MRI system 100 based on one or more other parameters (e.g., clinical needs) of an imaging process. The timing information may correspond to the type of the gradient and RF waveforms that are sent to the gradient coils 202 and the RF coils 203, respectively, so that the MR signals are correctly sampled. The processor 310 may also generate one or more MR images by reconstructing the sampled MR data.

The storage 320 may store data/information obtained from the scanner 110, the user device 130, the storage device 150, or any other component of the MRI system 100. In some embodiments, the storage 320 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing device 140 for generating one or more images based on MR data. In some embodiments, the storage 320 may store one or more reconstructed MRI images.

The I/O 330 may input or output signals, data, or information. In some embodiments, the I/O 330 may enable user interaction with the processing device 140. In some embodiments, the I/O 330 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 340 may be connected to a network (e.g., the network 120) to facilitate data communications. The communication port 340 may establish connections between the processing device 140 and the scanner 110, the user device 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 340 may be a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
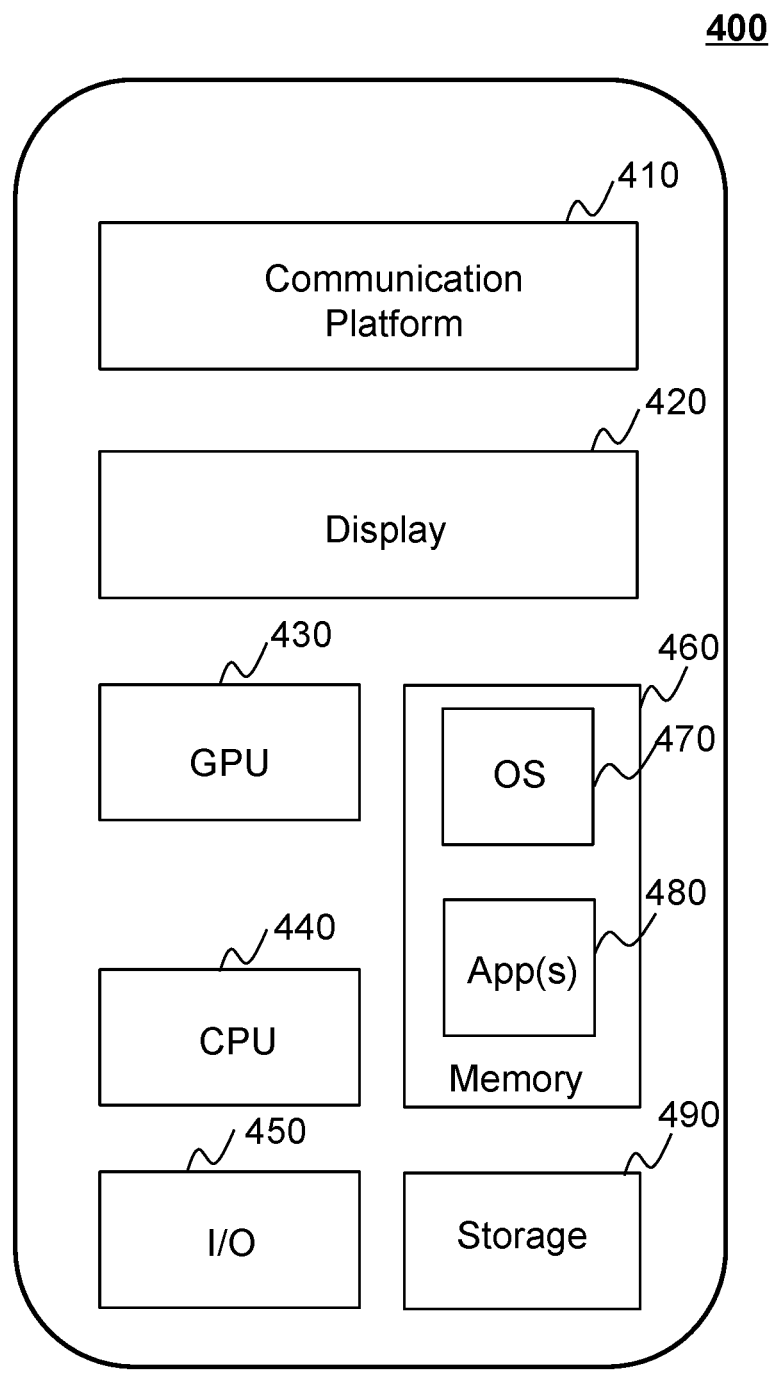
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device on which the user device 130 may be implemented according to some embodiments of the present disclosure. As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS, Android, Windows Phone, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 140. User interactions with the information stream may be achieved via the I/O 450 and provided to the processing device 140 and/or other components of the MRI system 100 via the network 120. Merely by way of example, a user (e.g., a doctor, a technician, an engineer, an operator, etc.) of the MRI system 100 may input data related to an object (e.g., a patient) that is being/to be imaged/scanned through the I/O 450. The data related to the object may include identification information (e.g., the name, age, gender, medical history, contact information, physical examination result, etc.) and/or the test information including the nature of the MRI scan that needs to be performed. The user may also input parameters needed for the operation of the scanner 110, such as image contrast and/or ratio, a region of interest (ROI), slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with steady-state procession, and so on), a flip angle value, acquisition time (TA), echo time (TE), repetition time (TR), inversion time (TI), saturation time (TS), echo train length (ETL), the number of phases, the number of excitations (NEX), bandwidth (e.g., RF receiver bandwidth, RF transmitter bandwidth, etc.), a scan type, a type of sampling, time points when the MR data is acquired (e.g., cardiac phases, respiratory phases, etc.), time points when an acquisition phase of the scan is triggered, a duration of a period of the acquisition phase, or the like, or any combination thereof. The I/O may also display MR images generated based on the sampled data.

In some embodiments, the I/O 450 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 5:
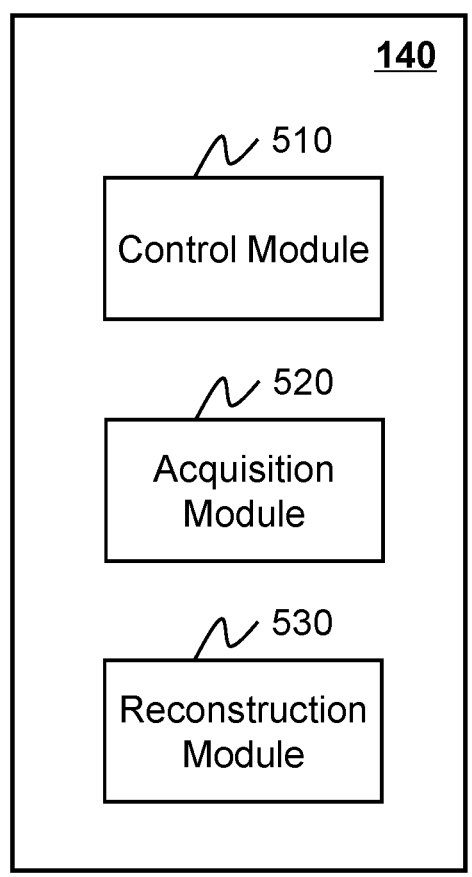
FIG. 5 is a schematic block diagram illustrating an exemplary processing device according to some embodiments of the present disclosure.

FIG. 5 is a schematic block diagram illustrating an exemplary processing device according to some embodiments of the present disclosure. In some embodiments, the processing device 140 may include an acquisition module 520 and a reconstruction module 530. In some embodiments, the processing device 140 may further include a control module 510.

The acquisition module 520 may obtain target k-space data related to an ROI of an object.

The reconstruction module 530 may generate, based on the target k-space data using a trained reconstruction model, one or more target images. The trained reconstruction model may be a machine learning model.

In some embodiments, the reconstruction module 530 may generate, based on the target k-space data using the trained reconstruction model, a target images corresponding to a target slice of the ROI. In some embodiments, the reconstruction module 530 may generate, based on the target k-space data using a trained reconstruction model, a plurality of target images (temporal frames) each of which corresponds to a same target slice of the ROI and one of a plurality of target acquisition periods. In some embodiments, the reconstruction module 530 may generate, based on the target k-space data using a trained reconstruction model, a plurality of target images each of which corresponds to one of a plurality of target slices of the ROI. In some embodiments, the reconstruction module 530 may generate, based on the target k-space data using a trained reconstruction model, a plurality of target images (temporal frames) each of which corresponds to one of a plurality of target slices of the ROI and one of a plurality of target acquisition periods.

The control module 510 may cause the scanner 110 to scan the ROI of the object. In some embodiment, the control module 510 may cause the scanner 110 to apply one or more multiband excitation radio frequency (RF) pulses to the ROI to simultaneously excite, for one or more times, the plurality of target slices of the ROI. In some embodiment, the control module 510 may cause the MRI device to apply phase modulation to at least one of the excited target slices by applying, to each of the at least one of the excited target slices, a transmit phase that varies with a plurality of target acquisition periods and/or a phase encoding direction.

The acquisition module 520 may acquire the target k-space data from the plurality of excited target slices of the ROI at the plurality of target acquisition periods.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units. For example, the reconstruction module 530 may be divided into a first unit configured to obtain a trained reconstruction model and a first unit configured to perform image reconstruction using the trained reconstruction model.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 5). The storage module may be configured to store data generated during any process performed by any component of the processing device 140. As another example, each of the components of the processing device 140 may include a storage device. Additionally or alternatively, the components of the processing device 140 may share a common storage device.

FIG. 6A is a flowchart illustrating an exemplary process for SMS imaging according to some embodiments of the present disclosure. In some embodiments, the process 600 may be implemented in the MRI system 100 illustrated in FIG. 1. For example, the process 600 may be stored in a storage device (e.g., the storage device 150, or the storage 320 of the processing device 140) as a form of instructions, and can be invoked and/or executed by the processing device 140 (e.g., the processor 310 of the processing device 140, or one or more modules in the processing device 140 illustrated in FIG. 5). The operations of the illustrated process 600 presented below are intended to be illustrative. In some embodiments, the process 600 may be accomplished with one or more additional operations not described, and/or without one or more of the operations discussed. Additionally, the order in which the operations of the process 600 as illustrated in FIG. 6A and described below is not intended to be limiting.

In 610, the processing device 140 (e.g., the control module 510) may cause an MRI device (e.g., the scanner 110) to apply one or more excitation radio frequency (RF) pulses to a region of interest (ROI) of an object (e.g., a patient) to simultaneously excite, for one or more times, a plurality of target slices of the ROI.

In some embodiments, the RF coils 203 may generate the one or more excitation RF pulses each of which is applied to the ROI to simultaneously excite a plurality of target slices of the ROI for one time. An excitation RF pulse may be applied in the presence of a slice-selective gradient in order to produce transverse magnetization in the plurality of target slice of the ROI.

In some embodiments, the excitation RF pulse may be a composite RF pulse including a plurality of excited bands each of which is used to excite one of the plurality of target slices. For example, each of the plurality of excited bands may be of a different frequency value and bandwidth corresponding to the slice location and/or thickness of one of the plurality of target slices so as to excite the corresponding target slice.

In 620, the processing device 140 (e.g., the control module 510) may cause the MRI device (e.g., the scanner 110) to apply phase modulation to at least one of the plurality of excited target slices by applying, to each of the at least one of the plurality of excited target slices, a transmit phase that varies with a plurality of target acquisition periods and/or a phase encoding direction.

In some embodiments, a target acquisition period may refer to a period in which target k-space data corresponding to an aliased image of the plurality of target slices is acquired. In some embodiments, in SMS imaging, k-space data corresponding to the plurality of target slices may be acquired simultaneously. Therefore, a target acquisition period may also refer to a period in which target k-space data corresponding to a target unaliased image (details regarding "target unaliased image" can be found in description in connection with operation 640) of one of the plurality of target slices. For example, the process 600 for SMS imaging may be used to generate a physiological motion cine of the ROI (e.g., a cine of the cardiac motion of a heart or the respiration motion of a lung). In this case, a series of unaliased image (e.g., temporal frames) each of which depicts one of the plurality of target slices corresponding to a motion phase (e.g., a cardiac phase such as cardiac diastole or cardiac systole, or a respiration phase such as end-expiration or end-inspiration) may be generated. A target acquisition period may correspond to a motion phase. As another example, the process 600 for SMS imaging may be used for perfusion analysis and indicating a change of a density of a contrast agent in the plurality of target slices over time. In this case, a series of unaliased image (e.g., temporal frames) each of which indicates a density of a contrast agent in one of the plurality of target slices at a time point may be generated. A target acquisition period may correspond to a time point of a time-density curve of the contrast agent.

In some embodiments, a transmit phase applied to a target slice may vary with the plurality of target acquisition periods. For example, transmit phases applied to k-space data corresponding to different target unaliased images (e.g., temporal frames) of a same target slice may be different. In some embodiments, the transmit phase applied to the target slice may further vary along a phase encoding direction. In some embodiments, one of the plurality of target slices may not be phase-modulated, e.g., not be applied to a transmit phase. In some embodiments, the transmit phases applied to two or more of the plurality of target slices may be different.

In some embodiments, a transmit phase applied to a target slice may include a plurality of phase profiles that are applied to the target slice corresponding to the plurality of target acquisition periods. For example, one of the plurality of phase profiles $\theta_{p,s}^l$ ($0 \leq \theta \leq 2\pi$) may be applied to a target slice s so that MR data (e.g., an echo) that is generated from the target slice s and filled into a phase encoding line/in a target acquisition period p is of a phase value corresponding to the phase profile $\theta_{p,s}^l$. In some embodiments, the phase profiles corresponding to the same target slice, the same target acquisition period, and two consecutive phase encoding lines may be different. For example, $\theta_{p,s}^l$ may be different from $\theta_{p,s}^{l+1}$. In some embodiments, the phase profiles corresponding to the same target slice and the same target acquisition period may be dynamically cycled as a function of phase encoding lines, e.g., $\theta_{p,s}^l = \theta_{p,s}^{l+\Delta l}$, wherein $\Delta l$ may be an arbitrary integer, and particularly, equal to the number (or count) of the plurality of target slices. In some embodiments, the phase profiles corresponding to the same target slice, the same phase encoding line, and two consecutive target acquisition periods may be different. For example, $\theta_{p,s}^l$ may be different from $\theta_{p+1,s}^l$. In some embodiments, the phase profiles corresponding to the same target slice and the same phase encoding line may be dynamically cycled as a function of the plurality of target acquisition periods, e.g., $\theta_{p+\Delta p,s}^l = \theta_{p,s}^l$, wherein $\Delta p$ may be an arbitrary integer, and particularly, equal to the number (or count) of the plurality of target slices. In some embodiments, $\theta_{p+\Delta,s}^{l} = \theta_{p,s}^{l+\Delta}$, wherein $\Delta$ may be an arbitrary integer.

In some embodiments, the transmit phases applied to two or more of the plurality of target slices may be with different variations over the phase encoding direction and/or the plurality of target acquisition periods.

In some embodiments, the application, to a target slice, of a transmit phase varying over the phase encoding direction and a plurality of target acquisition periods may achieve a field of view (FOV) shift of the target slice in image domain corresponding to each of the plurality of target acquisition periods, and the FOV shifts of the target slice corresponding to the plurality of target acquisition periods may be different. In some embodiments, the FOV shifts of the target slice corresponding to two consecutive target acquisition periods may be different. In some embodiments, the FOV shifts of the target slice corresponding to the plurality of target acquisition periods may be dynamically cycled as a function of the plurality of target acquisition periods. For example, the FOV shift of the target slice corresponding to the target acquisition period $P_1$ is FOV/3, the FOV shift of the target slice corresponding to the target acquisition period $P_2$ is 2FOV/3, the FOV shift of the target slice corresponding to the target acquisition period $P_3$ is FOV/3, and so on. In some embodiments, the FOV shifts of different phase-modulated target slices corresponding to the same target acquisition period may be different. For example, the FOV shift of the target slice $s_1$ corresponding to the target acquisition period $P_1$ is FOV/3, and the FOV shift of the target slice $s_2$ corresponding to the target acquisition period $P_1$ is 2FOV/3.

In some embodiments, the phase modulation of the at least one of the plurality of target slices may be realized by equipping the one or more excitation RF pulses with the phase profiles of the transmit phase applied to the at least one of the plurality of target slices. For example, for a phase profile corresponding to a phase encoding line, a target slice, and a target acquisition period, if the phase encoding line is acquired corresponding to the excitation of an excited band of an excitation RF pulse, the phase profile may be equipped in the excited band.

Details regarding the transmit phase may be found in, for example, the reference "Ferrazzi G, et al., Autocalibrated multiband CAIPIRINHA with through-time encoding: Proof of principle and application to cardiac tissue phase mapping, Magn Reson Med. 2019 February; 81(2):1016-1030," which is incorporated herein by reference.

In 630, the processing device 140 (e.g., the acquisition module 520) may acquire target k-space data (also referred to as autocalibration acquisition data) from the plurality of excited target slices of the ROI at the plurality of target acquisition periods.

In some embodiments, following excitation of the nuclear spins in the plurality of target slices, target k-space data may be acquired by sampling a series of echo signals generated from the plurality of excited target slices in the presence of a plurality of readout gradients (also referred to as frequency encoding gradients) and a plurality of phase encoding gradients. A readout gradient may act to fill an echo signal into the k-space along the frequency-encoding direction. The spatial encoding of an echo signal along the phase-encoding direction may be performed by a phase encoding gradient. The phase-encoding gradient may act to determine a filling position (e.g., a phase encoding line) of an echo signal in the k-space along the phase encoding direction.

In some embodiments, the k-space may be undersapmed, fully sampled, or oversampled to obtain the target k-space data. In some embodiments, the trajectory of the target k-space data may include a Cartesian trajectory or a non-Cartesian trajectory such as radial lines and spirals.

In some embodiments, a pulse sequence may include an excitation pulse RF, a slice-selective gradient, one or more readout gradients, and one or more phase encoding gradients illustrated above. The pulse sequence may be repeated one or more times such that the target k-space data are acquired. In some embodiments, the pulse sequence may include gradient-recalled echo (GRE), balanced steady-state free precession (bSSFP), fast spin-echo (FSE), echo-planer imaging (EPI), etc.

In some embodiments, the target k-space data may include a plurality of first k-space data sets each of which corresponds to the plurality of target slices and one of the plurality of target acquisition periods. A first k-space data set may be an aliased k-space data set that including k-space data from the plurality of target slices corresponding to one of the plurality of target acquisition periods. An aliased image of the plurality of target slices corresponding to one of the plurality of target acquisition periods may be obtained by performing inverse Fourier transform on the corresponding first k-space data set.

In some embodiments, after the plurality of target slices are simultaneously excited, a plurality of sets of echo signals may be generated from the plurality of excited target slices in sequence. Each of the plurality of sets of echo signals may include a plurality echo signals that are simultaneously generated from the plurality of excited target slices, respectively. Under the effect of the readout gradients and the phase encoding gradients, the echo signals simultaneously generated from the plurality of target slices may be filled into the same position (e.g., a phase encoding line) in the k-space. In this way, when the filing of the k-space is finished, the acquired k-space data may be referred to as a first k-space data set of the target k-space data. The period in which the first k-space data set is acquired may be referred to as a target acquisition period.

In some embodiments, the plurality of first k-space data sets may be acquired in sequence. For example, after the acquisition of a first k-space data set is finished, the acquisition of anther first k-space data set may start. In some embodiments, the plurality of first k-space data sets may be acquired in parallel. For example, for cardiac cine imaging, in a first cardiac cycle, echo signals generated corresponding to a first cardiac phase may be filled into a first k-space, and echo signals generated corresponding to a second cardiac phase subsequent to the first cardiac phase in the first cardiac cycle may be filled into a second k-space. In a second cardiac cycle subsequent to the first cardiac cycle, echo signals generated corresponding to the first cardiac phase may be filled into the first k-space, and echo signals generated corresponding to the second cardiac phase may be filled into the second k-space. In this way, a first k-space data set 1 may be obtained by filling the first k-space, and a first k-space data set 2 may be obtained by filling the second k-space. The first k-space data set 1 and the first k-space data set 2 may be acquired in parallel. The first k-space data set 1 may correspond to the first cardiac phase, and the first k-space data set 2 may correspond to the second cardiac phase.

In some embodiments, a period between two consecutive excitation RF pulses may be referred to as a repetition time (TR). There may be any correspondence between a TR and a target acquisition period. For example, a TR may include one or more target acquisition periods, indicating that one or more first k-space data sets may be acquired within a TR. As another example, different portions of a target acquisition period may be distributed in more than one TRs, indicating that a first k-space data set corresponding to the target acquisition period may be acquired within more than one TR.

FIGS. 6B and 6C are schematic diagrams illustrating exemplary acquisition of target k-space data according to some embodiments of the present disclosure.

As shown in FIG. 6B, three target slices, $s_1$, $s_2$, and $s_3$, are simultaneously excited. Target k-space data may be acquired from $s_1$, $s_2$, and $s_3$ in a first target acquisition period $P_1$ and a second target acquisition period $P_2$. The target k-space data may include a first k-space data set $D_1$ that is acquired from $s_1$, $s_2$, and $s_3$ by filling a first k-space $K_1$ in $P_1$ and a first k-space data set $D_2$ that is acquired from $s_1$, $s_2$, and $s_3$ by filling a second k-space $K_2$ in $P_2$. Slice $s_1$ may not be phase-modulated, e.g., not be applied to any transmit phase, in $P_1$ and $P_2$. Slice $s_2$ may be phase-modulated by being applied to a first transmit phase that varies over spatial dimension, e.g., the phase encoding direction, and the temporal dimension, e.g., $P_1$ and $P_2$. Slice $s_3$ may be phase-modulated by being applied to a second transmit phase that varies over spatial dimension, e.g., the phase encoding direction, and the temporal dimension, e.g., $P_1$ and $P_2$. The first transmit phase may be different from the second transmit phase.

In some embodiments, the first k-space data set $D_1$ and the first k-space data set $D_2$ may be acquired in sequence. For example, as shown in FIG. 6B, after $s_1$, $s_2$, and $s_3$ are simultaneously excited, three echo signals $echo_{s_1}^1$, $echo_{s_2}^1$, and $echo_{s_3}^1$ may be simultaneously generated from $s_1$, $s_2$, and $s_3$, respectively. Echo signal $echo_{s_1}^1$ may not be applied to any phase profile, $echo_{s_2}^1$ may be applied to a phase profile $\theta_{p_1,s_2}^{l_1}$, and $echo_{s_3}^1$ may be applied to a phase profile $\theta_{p_1,s_3}^{l_1}$, Under the effect of a readout gradient and a phase encoding gradient, $echo_{s_1}^1$ with no phase modulation, $echo_{s_2}^1$ with the phase $\theta_{p_1,s_2}^{l_1}$ and $echo_{s_3}^1$ with the phase $\theta_{p_1,s_3}^{l_1}$ may be filled into the same position (e.g., the phase encoding line $l_1$) of the first k-space $K_1$. Subsequently, another three echo signals $echo_{s_1}^2$, $echo_{s_2}^2$, and $echo_{s_3}^2$ may be simultaneously generated from $s_1$, $s_2$, and $s_3$, respectively. Echo signal $echo_{s_1}^2$ may not be applied to any phase profile, $echo_{s_2}^2$ may be applied to a phase profile $\theta_{p_1,s_2}^{l_2}$, and $echo_{s_3}^1$ may be applied to a phase profile $\theta_{p_1,s_3}^{l_2}$. Under the effect of a readout gradient and a phase encoding gradient, $echo_{s_1}^2$ with no phase modulation, $echo_{s_2}^2$ with the phase $\theta_{p_1,s_2}^{l_2}$, and $echo_{s_3}^2$ with the phase $\theta_{p_1,s_2}^{l_2}$ may be filled into the same position (e.g., the phase encoding line $l_2$) of the first k-space $K_1$. The first k-space may be sampled in the above way to acquire the first k-space data set $D_1$ in $P_1$.

After the acquisition of the first k-space data set $D_1$ is finished, the acquisition of the first k-space data set $D_2$ is started. For three echo signals $echo_{s_1}^3$, $echo_{s_1}^3$, and $echo_{s_3}^3$ simultaneously generated from $s_1$, $s_2$, and $s_3$, respectively, echo may not be applied to any phase profile, $echo_{s_2}^3$ may be applied to a phase profile $\theta_{p_2,s_2}^{l_1}$, and $echo_{s_3}^3$ may be applied to a phase profile $\theta_{p_2,s_3}^{l_1}$, Under the effect of a readout gradient and a phase encoding gradient, $echo_{s_1}^3$ with no phase modulation, $echo_{s_2}^3$ with the phase $\theta_{p_2,s_2}^{l_1}$ and $echo_{s_3}^3$ with the phase $\theta_{p_2,s_3}^{l_1}$ may be filled into the same position (e.g., the phase encoding line $l_1$) of the second k-space $K_2$. Subsequently, another three echo signals $echo_{s_1}^4$, $echo_{s_2}^4$, and $echo_{s_3}^4$ may be simultaneously generated from $s_1$, $s_2$, and $s_3$, respectively. Echo signal $echo_{s_1}^4$ may not be applied to any phase profile, $echo_{s_2}^4$ may be applied to a phase profile $\theta_{p_2,s_2}^{l_2}$, and $echo_{s_3}^4$ may be applied to a phase profile $\theta_{p_2,s_3}^{l_2}$. Under the effect of a readout gradient and a phase encoding gradient, $echo_{s_1}^4$ with no phase modulation, $echo_{s_2}^4$ with the phase $\theta_{p_2,s_2}^{l_2}$, and $echo_{s_3}^4$ with the phase $\theta_{p_2,s_3}^{l_2}$ may be filled into the same position (e.g., the phase encoding line $l_2$) of the second k-space $K_2$. The second k-space may be sampled in the above way to acquire the first k-space data set $D_2$ in $P_2$.

Alternatively, the first k-space data set $D_1$ and the first k-space data set $D_2$ may be acquired in parallel. For example, for cardiac cine imaging, as shown in FIG. 6B, after $s_1$, $s_2$, and $s_3$ are simultaneously excited, three echo signals $echo_{s_1}^1$, $echo_{s_2}^1$, and $echo_{s_3}^1$ may be simultaneously generated corresponding to a first cardiac phase in a first cardiac cycle from $s_1$, $s_2$, and $s_3$, respectively. Echo signal $echo_{s_1}^1$ may not be applied to any phase profile, $echo_{s_2}^1$ may be applied to a phase profile $\theta_{p_1,s_2}^{l_1}$, and $echo_{s_3}^1$ may be applied to a phase profile $\theta_{p_2,s_3}^{l_1}$. Under the effect of a readout gradient and a phase encoding gradient, $echo_{s_1}^1$ with no phase modulation, $echo_{s_2}^1$ with the phase $\theta_{p_1,s_2}^{l_1}$, and $echo_{s_3}^1$ with the phase $\theta_{p_1,s_3}^{l_1}$ may be filled into the same position (e.g., the phase encoding line $l_1$) of the first k-space Subsequently, another three echo signals $echo_{s_1}^2$, $echo_{s_2}^2$, and $echo_{s_3}^2$ may be simultaneously generated corresponding to a first cardiac phase in the first cardiac cycle from $s_1$, $s_2$, and $s_3$, respectively. Echo signal $echo_{s_1}^2$ may not be applied to any phase profile, $echo_{s_2}^2$ may be applied to a phase profile $\theta_{p_2,s_2}^{l_1}$, and $echo_{s_3}^2$ may be applied to a phase profile $\theta_{p_2,s_3}^{l_1}$. Under the effect of a readout gradient and a phase encoding gradient, $echo_{s_1}^2$ with no phase modulation, $echo_{s_2}^2$ with the phase $\theta_{p_2,s_2}^{l_1}$ and $echo_{s_3}^2$ with the phase $\theta_{p_2,s_3}^{l_1}$ may be filled into the same position (e.g., the phase encoding line $l_1$) of the second k-space $K_2$.

For three echo signals $echo_{s_1}^3$, $echo_{s_2}^3$, and $echo_{s_3}^3$ simultaneously generated corresponding to the first cardiac phase in a second cardiac cycle from $s_1$, $s_2$, and $s_3$, respectively, $echo_{s_1}^3$ may not be applied to any phase profile, $echo_{s_2}^3$ may be applied to a phase profile $\theta_{p_1,s_2}^{l_2}$, and $echo_{s_3}^3$ may be applied to a phase profile $\theta_{p_1,s_3}^{l_2}$. Under the effect of a readout gradient and a phase encoding gradient, $echo_{s_1}^3$ with no phase modulation, $echo_{s_2}^3$ with the phase $\theta_{p_1,s_2}^{l_2}$, and $echo_{s_3}^3$ with the phase $\theta_{p_1,s_3}^{l_2}$ may be filled into the same position (e.g., the phase encoding line $l_2$) of the first k-space Kt. Subsequently, another three echo signals $echo_{s_1}^4$, $echo_{s_2}^4$, and $echo_{s_3}^4$ may be simultaneously generated corresponding to the second cardiac phase in the second cardiac cycle from $s_1$, $s_2$, and $s_3$, respectively. Echo signal $echo_{s_1}^4$ may not be applied to any phase profile, $echo_{s_2}^4$ may be applied to a phase profile $\theta_{p_2,s_2}^{l_2}$, and $echo_{s_3}^4$ may be applied to a phase profile $\theta_{p_2,s_3}^{l_2}$. Under the effect of a readout gradient and a phase encoding gradient, $echo_{s_1}^4$ with no phase modulation, $echo_{s_2}^4$ with the phase $\theta_{p_2,s_2}^{l_2}$, and $echo_{s_3}^4$ with the phase $\theta_{p_2,s_3}^{l_2}$ may be filled into the same position (e.g., the phase encoding line $l_2$) of the second k-space $K_2$. The first k-space $K_1$ and the second k-space $K_2$ may be sampled in parallel in the above way to acquire the first k-space data set $D_1$ in $P_1$ (corresponding to the first cardiac phase) and the first k-space data set $D_2$ in $P_2$ (corresponding to the second cardiac phase).

In some embodiments, $s_2$ may be phase-modulated by being applied to a first transmit phase that varies over spatial dimension, e.g., the phase encoding direction, and the temporal dimension, e.g., $P_1$ and $P_2$. For example, the first transmit phase may include phase profiles $\theta_{p_1,s_2}^{l_1}$, $\theta_{p_1,s_2}^{l_2}$, $\theta_{p_2,s_2}^{l_1}$, and $\theta_{p_2,s_2}^{l_2}$, $\theta\theta_{p_1,s_1}^{l_1}$ may be different from $\theta_{p_1,s_2}^{l_2}$ and $\theta\theta_{p_1,s_2}^{l_1}$ may be different from $\theta_{p_2,s_2}^{l_1}$. In some embodiments, $s_3$ may be phase-modulated by being applied to a second transmit phase that varies over spatial dimension, e.g., the phase encoding direction, and the temporal dimension, e.g., $P_1$ and $P_2$. For example, the second transmit phase may include phase profiles $\theta_{p_1,s_3}^{l_1}$, $\theta_{p_1,s_3}^{l_2}$, $\theta_{p_2,s_2}^{l_1}$, and $\theta_{p_2,s_3}^{l_2}$. $\theta_{p_1,s_3}^{l_1}$ may be different from $\theta_{p_1,s_3}^{l_2}$ and $\theta_{p_1,s_3}^{l_1}$ may be different from $\theta_{p_2,s_3}^{l_1}$. In some embodiments, the first transmit phase may be different from the second transmit phase. For example, the variation of $\theta_{p_1,s_2}^{l_1}$, $\theta_{p_1,s_2}^{l_2}$, $\theta_{p_2,s_2}^{l_1}$, and $\theta_{p_2,s_2}^{l_2}$ may be different from the variation of $\theta_{p_1,s_3}^{l_1}$, $\theta_{p_1,s_3}^{l_2}$, $\theta_{p_2,s_3}^{l_1}$, and $\theta_{p_2,s_3}^{l_2}$.

In some embodiments, the acquisition of the target k-space data may be implemented on a single or multiple channel receiver coil.

In 640, the processing device 140 (e.g., the reconstruction module 530) may generate, based on the target k-space data using a trained reconstruction model, a plurality of target unaliased images each of which corresponds to one of the plurality of target slices and one of the plurality of target acquisition periods. For example, the process 600 for SMS imaging may be used to generate a physiological motion cine of the ROI (e.g., a cine of the cardiac motion of a heart or the respiration motion of a lung). In this case, a series of target unaliased image (e.g., temporal frames) each of which depicts one of the plurality of target slices corresponding to a motion phase (e.g., a cardiac phase such as cardiac diastole or cardiac systole, or a respiration phase such as end-expiration or end-inspiration) may be generated. A target acquisition period may correspond to a temporal frame and the corresponding motion phase. As another example, the process 600 for SMS imaging may be used for perfusion analysis and indicating a change of a density of a contrast agent in the plurality of target slices over time. In this case, a series of unaliased image (e.g., temporal frames) each of which indicates a density of a contrast agent in one of the plurality of target slices at a time point may be generated. A target acquisition period may correspond to the temporal frame and the corresponding time point.

In some embodiments, compared with the imaging that only excites a single slice one time, SMS excites multiple slices at the same time and simultaneously acquires magnetic resonance (MR) signals generated from the multiple excited slices. The MR signals are filled into the k-space to generate k-space data. Because the received MR signals include the contributions of the multiple excited slices, reconstruction of the k-space data directly using inverse Fourier transform may lead to an aliased image of the multiple slices. As used in the present disclosure, the term "target unaliased image," also referred to as "target image," refers to an image corresponding to a single slice of the multiple simultaneously excited slices, which is less aliased or unaliased relative to the aliased image of the multiple slices.

In some embodiments, the trained reconstruction model may include a machine learning model or other forms of computer intelligence. In some embodiments, the trained reconstruction model may include a deep learning model. In some embodiments, the trained reconstruction model may include a neural network model. In some embodiments, the trained reconstruction model may include a convolutional neural network (CNN), a U-net, a V-net, and a recurrent neural network (RNN), or the like, or any combination thereof.

In some embodiments, the target k-space data may be input into the trained reconstruction model, and the trained reconstruction model may output the plurality of target unaliased images based on the target k-space data.

In some embodiments, the processing device 140 may generate a plurality of target aliased images by performing inverse Fourier transform on the target k-space data. Each of the plurality of target aliased images may correspond to the plurality of target slices and one of the plurality of target acquisition periods. For example, the target k-space data may include a plurality of first k-space data sets each of which corresponds to the plurality of target slices and one of the plurality of target acquisition periods. The processing device 140 may generate the plurality of target aliased images by performing inverse Fourier transform on the plurality of first k-space data sets, respectively. The processing device 140 may input the plurality of aliased images into the trained reconstruction model. The trained reconstruction model may output the plurality of target unaliased images based on the plurality of target aliased images.

In some embodiments, the processing device 140 may determine a plurality of reference data sets based on the target k-space data. Each of the plurality of reference data sets may correspond to one of the plurality of target slices and one of the plurality of target acquisition periods. The plurality of reference data sets may provide unaliased information for unaliasing of the plurality of target slices in the target k-space data.

In some embodiments, for a target acquisition period A, the processing device 140 may combine two or more first k-space data sets corresponding to two or more consecutive target acquisition periods including the target acquisition period A to generate separated data sets each of which corresponds to one of the plurality of target slices and the target acquisition period A. Subsequently, the processing device 140 may generate the reference data sets by applying phase modulation similar to what is illustrated in operation 620 by multiplying the corresponding separated data sets with the at least one transmit phase to match the phase modulation of the target k-space data.

In some embodiments, the processing device 140 may generate the reference data sets using another method. For example, the processing device 140 may generate an averaged data set by averaging the separated data sets corresponding to the plurality of target acquisition periods. The processing device 140 may generate the reference data sets from the averaged data set.

Details regarding determining the reference data sets based on the target k-space data may be found in, for example, the reference "Ferrazzi G, et al., Autocalibrated multiband CAIPIRINHA with through-time encoding: Proof of principle and application to cardiac tissue phase mapping, Magn Reson Med. 2019 February; 81(2):1016-1030," which is incorporated herein by reference.

In some embodiments, the processing device 140 may generate, based on the target k-space data and the plurality of reference data sets, the plurality of target unaliased images using the trained reconstruction model. For example, the processing device 140 may generate a plurality of aliasing images each of which corresponds to the plurality of target slices and one of the plurality of target acquisition periods by performing inverse Fourier transform on the target k-space data. The processing device 140 may generate a plurality of reference images with low image resolution by performing inverse Fourier transform on the reference data sets. The processing device 140 may input the plurality of aliasing images and the plurality of reference images into the trained reconstruction model. The trained reconstruction model may output the plurality of unaliased images based on the plurality of aliasing images and the plurality of reference images.

As another example, the processing device 140 may input the target k-space data and the plurality of reference data sets into the trained reconstruction model. The trained reconstruction model may output the plurality of unaliased images based on the target k-space data and the plurality of reference data sets.

Figure 6D:
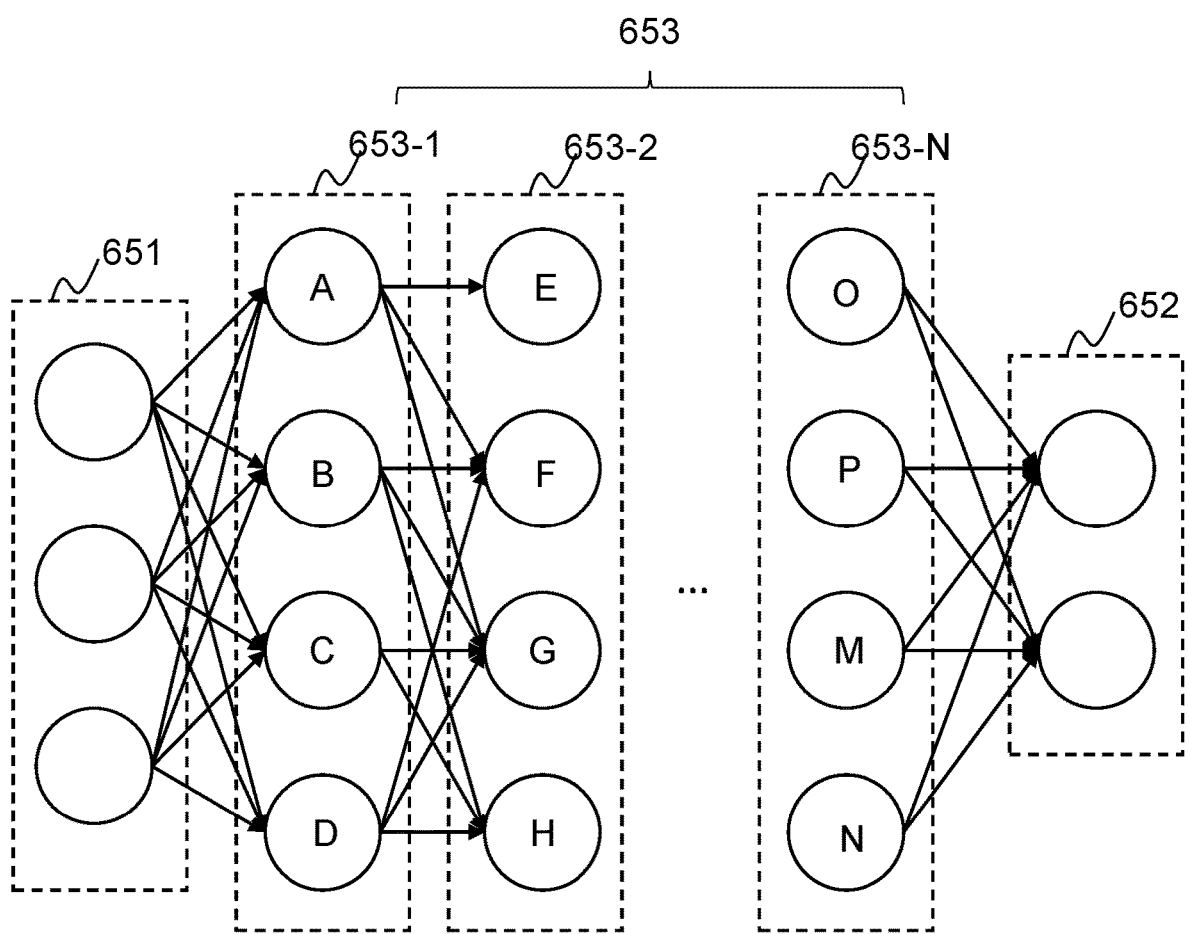
FIG. 6D is a schematic diagram illustrating an exemplary trained reconstruction model according to some embodiments of the present disclosure.

FIG. 6D is a schematic diagram illustrating an exemplary trained reconstruction model 650 according to some embodiments of the present disclosure.

As shown in FIG. 6D, the trained reconstruction model 650 may include an input layer 651, an output layer 652, and a plurality of hidden layers 653. The layers of the trained reconstruction model 650 may be connected in a feed-forward fashion, and an output of an $i^{th}$ layer may be provided as an input to an $(1 \pm 1)^{th}$ layer. In some embodiments, in the trained reconstruction model 650, the input layer 651 may be configured to receive input data (e.g., the target k-space data, the plurality of aliased images, the plurality of reference data sets, or the plurality of reference images) of the trained reconstruction model 650. Each hidden layer (e.g., 653-1, 653-2, . . . , 653-N, etc.) may perform a specific function, e.g., convolution, pooling, normalization, matrix multiplication, non-linear activation, or the like. The output layer 652 may receive an input from the preceding layer and apply one or more transformations to the received input to generate output data (e.g., the plurality of target unaliased images) of the trained reconstruction model 650. In some embodiments, the trained reconstruction model 650 may operate by managing coefficients of a weighting function that converts the input data into the output data. The weighting function may be represented as the plurality of hidden layers 653 between the input layer 651 and the output layer 652 of the trained reconstruction model 650. In some embodiments, each node (e.g., A-N in FIG. 6D) of the plurality of hidden layers 653 may read the input data, multiplies by various weights or coefficients, and produces the output data.

For illustration purposes, a convolutional neural network (CNN) model may be taken as an example. Exemplary hidden layers may include a convolutional layer, a pooling layer, and a fully connected layer. In some embodiments, input data such as k-space data (e.g., the target k-space data and/or the plurality of reference data sets) or one or more images (e.g., the plurality of aliased images and/or the plurality of reference images) may be inputted into the trained reconstruction model. The k-space data or the one or more images may be represented as a 2D matrix or a 3D matrix including a plurality of elements (e.g., pixels or voxels). Each of the plurality of elements in the matrix may have a value representing a feature or characteristic of the element.

The convolutional layer may include one or more kernels, which may be used to extract a feature of the input data. In some embodiments, each of the one or more convolutional kernel may have a specific size and stride. In some embodiments, each of the one or more kernels may filter a portion of the input data to generate a specific feature corresponding to the portion. The specific feature may be determined based on the one or more kernels. Exemplary features may include a low-level feature (e.g., an edge feature, a textural feature, a pixel value feature), a high-level feature, or a complicated feature.

The pooling layer may take an output of the convolutional layer as an input. The pooling layer may include a plurality of pooling nodes, which may be used to sample the output of the convolutional layer, so as to reduce the computational load of data processing and accelerate the speed of data processing speed. In some embodiments, a size of the matrix representing the input data may be reduced in the pooling layer.

The fully connected layer may include a plurality of neurons. The neurons may be connected to the pooling nodes in the pooling layer. In the fully connected layer, a plurality of vectors corresponding to the plurality of pooling nodes may be determined based on one or more features of the input data, and a plurality of weighting coefficients may be assigned to the plurality of vectors.

The output layer may determine an output based on the vectors and the weighting coefficients obtained from the fully connected layer. In some embodiments, an output of the output layer may include the plurality of target unaliased images.

In some embodiments, the trained reconstruction model may be implemented on one or more processing devices (e.g., the processing device 140, the processor 210, the terminal 130, the CPU 340, the GPU 330, etc.). For example, one or more layers may be respectively implemented on a processing device. As another example, one or more components of a layer may be implemented on a same processing device. In some embodiments, a plurality of processing devices may execute a parallel processing operation in some layers of the trained reconstruction model by, for example, assigning two or more processing devices for an operation of different nodes (e.g., a kernel, a pooling node, a neuron) in the trained reconstruction model. For example, a first GPU may execute the operation corresponding to kernel A and kernel B, and a second kernel may execute the operation corresponding to kernel C and kernel D. Similarly, a plurality of GPUs may also execute the operation of other nodes (e.g., a kernel, a pooling node, a neuron) in the trained reconstruction model.

In addition, in some embodiments, a storage device (e.g., the storage device 150, the storage 320, the storage 490, the memory 460, etc.) may be provided for storing data related to the trained reconstruction model, such as an activation functions, a learned weight for each node, and/or a network topology (e.g., a number (or count) of the hidden layers, a type of each hidden layer, etc.). Optionally, the storage device may further store a training data set.

Traditional reconstruction methods for SMS imaging may be performed either in image domain using a least-squares approach (e.g., sensitivity encoding algorithm (SENSE)) or in k-space using a linear approach (e.g., generalized auto-calibrating partially parallel acquisitions (GRAPPA)). In comparison, the reconstruction for SMS imaging using a machine learning model is a non-linear approach, which may improve image quality and reconstruction speed.

In some embodiments, the reconstruction method using a machine learning model in the present disclosure may be applied in phase-modulated (as illustrated in operation 620) SMS imaging of a series dynamic images.

For example, the reconstruction method using a machine learning model in the present disclosure may be applied in reconstruction of a physiological motion (e.g., a cardiac motion or a respiration motion) cine of an ROI (e.g., at least a portion of a heart or a lung). In this case, each of the plurality of target acquisition periods may correspond to a physiological motion phase (e.g., a cardiac phase or a respiration phase) of the ROI, and the plurality of target unaliased images may form a physiological motion cine of the ROI.

As another example, the reconstruction method using a machine learning model in the present disclosure may be applied in perfusion imaging. In this case, the plurality of target unaliased images may be used for perfusion analysis and indicate a change of a density of a contrast agent in the plurality of target slices over time, and a target acquisition period may correspond to a time point in the time-density curve of the contrast agent in the plurality of target slices.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 7 is a flowchart illustrating an exemplary process for obtaining a trained reconstruction model according to some embodiments of the present disclosure. In some embodiments, the process 700 may be implemented in the MRI system 100 illustrated in FIG. 1. For example, the process 700 may be stored in a storage device (e.g., the storage device 150, or the storage 320 of the processing device 140) as a form of instructions, and can be invoked and/or executed by the processing device 140 (e.g., the processor 310 of the processing device 140, or one or more modules in the processing device 140 illustrated in FIG. 5). The operations of the illustrated process 700 presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 710, the reconstruction module 530 may obtain a plurality of training data sets. Each of the plurality of training data sets may include sample k-space data and a plurality of sample images.

In some embodiments, each of the plurality of sample images may correspond to one of a plurality of sample slices of a sample and one of a plurality of sample acquisition periods. As used in the present disclosure, the term "sample image," also referred to as "sample unaliased image," refers to an image corresponding to a single slice of the plurality of sample slices of the sample, which is less aliased or unaliased relative to an aliased image of the plurality of sample slices.

In some embodiments, the corresponding sample k-space data for each of at least one of the plurality of sample slices may be phase-modulated. In some embodiments, for each of at least one of the plurality of sample slices, phases of the corresponding sample k-space data may vary based on the plurality of sample acquisition periods. In some embodiments, for each of at least one of the plurality of sample slices, phases of the corresponding sample k-space data may further vary along the phase encoding direction. In some embodiments, modulated phases of the sample k-space data corresponding to two or more slices may be different.

In some embodiments, the sample k-space data may include a plurality of second k-space data sets each of which corresponds to the plurality of sample slices and one of the plurality of sample acquisition periods. A second k-space data set may be an aliased k-space data set that includes k-space data from the plurality of sample slices corresponding to one of the plurality of sample acquisition periods.

In some embodiments, the sample k-space data may include real k-space data that is acquired by simultaneously exciting the plurality of sample slices. The at least one of the excited sample slices may be applied to phase modulation by applying, to each of the at least one of the excited sample slices, a sample phase that varies with the plurality of target acquisition periods. In some embodiments, the sample phase may further vary along a phase encoding direction. In some embodiments, the sample phases applied to two or more of the plurality of sample slices may be different. In some embodiments, the sample k-space data may be acquired from the plurality of sample slices at the plurality of sample acquisition periods. The plurality of sample images may be generated from the sample k-space data using any reconstruction algorithm (e.g., SENSE, GRAPPA, etc.). In some embodiments, the sample k-space data may be undersampled, oversampled, or fully sampled.

In some embodiments, the sample k-space data may include synthesized k-space data. In this case, the plurality of sample images may be generated based on SMS imaging or single slice excitation imaging. A plurality of sample k-space data sets may be obtained by performing Fourier transform on the plurality of sample images. Each of the plurality of sample k-space data sets may correspond to one of the plurality of sample images. Phase modulation may be applied to the sample k-space data sets corresponding to at least one of the plurality of sample slices and the plurality of sample acquisition periods. For example, for each of the at least one of the plurality of sample slices, a sample phase varying based on the plurality of sample acquisition periods may be applied to the corresponding sample k-space data sets. In some embodiments, the sample phase may further vary along a phase encoding direction. In some embodiments, the sample phases applied to the sample k-space data sets corresponding to two or more of the plurality of sample slices may be different. In some embodiments, after phase modulation, the sample k-space data sets corresponding to the same sample acquisition period may be combined to obtain a second k-space data set. The second k-space data sets each of which corresponds to the plurality of sample slices and one of the plurality of sample acquisition periods may form the sample k-space data.

In some embodiments, the synthesized k-space data may be obtained further by applying an undersampling strategy to the plurality of second k-space data sets by replacing a portion of data in the plurality of second k-space data sets with zero. In some embodiments, the synthesized k-space data may be obtained further by applying an undersampling strategy to the plurality of sample k-space data sets by replacing a portion of data in the plurality of sample k-space data sets with zero. For example, for the sample k-space data sets corresponding to the plurality of sample slices and a sample acquisition period, a same undersampling strategy may be applied to the plurality of sample k-space data sets by replacing a portion of data in the same k-space position with zero.

In 720, the reconstruction module 530 may obtain the trained reconstruction model by training a preliminary model based on the plurality of training data sets.

In some embodiments, the reconstruction module 530 may obtain the trained reconstruction model by training a preliminary model using the sample k-space data and the sample images in the plurality of training data sets.

In some embodiments, for each of at least one of the plurality of training data sets, the reconstruction module 530 may generate a plurality of sample aliased images by performing inverse Fourier transform on the plurality of second k-space data sets of the sample k-space data in the training data set. Each of the plurality of sample aliased images may correspond to the plurality of sample slices and one of the plurality of sample acquisition periods.

In some embodiments, the reconstruction module 530 may obtain the trained reconstruction model by training the preliminary model based on the plurality of sample aliased images of the each of the at least one of the plurality of training data sets. For example, if the sample k-space data in all of the plurality of training data sets is transformed into the sample aliased images, the reconstruction module 530 may obtain the trained reconstruction model by training the preliminary model using the sample aliased images and the sample images in the plurality of training data sets. As another example, if the sample k-space data in a portion of the plurality of training data sets is transformed into the sample aliased images, the reconstruction module 530 may obtain the trained reconstruction model by training the preliminary model using the sample aliased images, the remain sample k-space data, and the sample images in the plurality of training data sets.

In some embodiments, during a training process of the trained reconstruction model, a preliminary model may be obtained. The preliminary model may be trained based on training input data (e.g., the sample k-space data and/or the sample aliased images) and the sample images (e.g., a known output (ground truth) of the training input data) of the plurality of training data sets to obtain the trained reconstruction model. In some embodiments, the preliminary model may include a plurality of weight parameters that are to be determined during learning, which may be referred to as a training process. In the training process, a training input may be processed by the preliminary model so that the preliminary model may learn how to provide an output for new input data by generalizing the information it learns in the training process from the training data. The purpose of learning may be to adapt the weight parameters on the incoming connections to predict the correct output when given an input.

Figure 8:
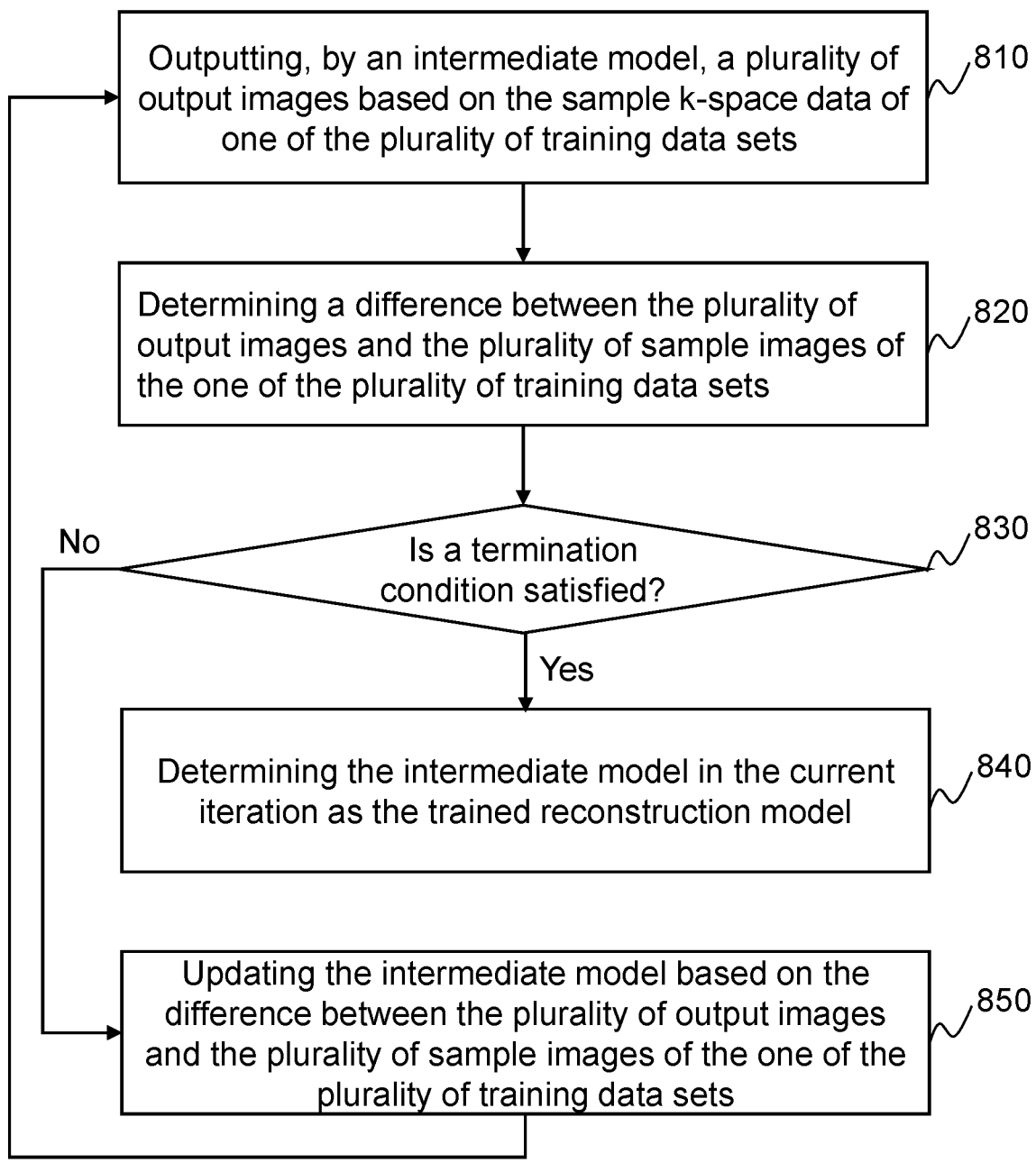
FIG. 8 is a flowchart illustrating an exemplary training process for obtaining a trained reconstruction model according to some embodiments of the present disclosure.

Details regarding the training process of the trained reconstruction model may be found elsewhere in the present disclosure (e.g., the description in connection with FIG. 8).

In some embodiments, after additional sample images are collected, the training process may be repeated to update the trained reconstruction model using the additional sample images with or without previous sample images used for earlier rounds of the training.

In some embodiments, the trained reconstruction model may be determined by the MRI system 100 (e.g., the processing device 140, the terminal 130, a storage device (the storage device 150, the storage 320, the storage 490)) or a third party (e.g., an external device). In some embodiments, the MRI system 100 may determine and/or update the trained reconstruction model offline and store the trained reconstruction model in the storage device. In some embodiments, the trained reconstruction model may be determined and/or updated (or maintained) by, e.g., the manufacturer of the scanner 110 or a vendor. For instance, the manufacturer or the vendor may load either one of the trained reconstruction model into the MRI system 100 or a portion thereof (e.g., the processing device 140 and/or the terminal 130) before or during the installation of the scanner 110, the processing device 140, and/or the terminal 130, and maintain or update the trained reconstruction model from time to time (periodically or not). The maintenance or update may be achieved by installing a program stored on a storage device (e.g., a compact disc, a USB drive, etc.) or retrieved from an external source (e.g., a server maintained by the manufacturer or vendor) via the network 120. The program may include a new model (e.g., a new trained reconstruction model) or a portion of a model that substitute or supplement a corresponding portion of the model.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 8 is a flowchart illustrating an exemplary training process for obtaining a trained reconstruction model according to some embodiments of the present disclosure. In some embodiments, the process 800 may be implemented in the imaging system 100 illustrated in FIG. 1. For example, the process 800 may be stored in a storage medium (e.g., the storage device 150, or the storage 320 of the processing device 140, the storage 490 of the terminal 130, the memory 460 of the terminal 130) as a form of instructions, and can be invoked and/or executed by the processing device 140 or the terminal 130 (e.g., the processor 310 of the processing device 140, the CPU 440 and/or the GPU 430 of the terminal 130, or one or more modules in the processing device 140 illustrated in FIG. 5). The operations of the illustrated process 800 presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting. In some embodiments, operation 720 of the process 700 may be performed based on the process 800.

In some embodiments, the reconstruction module 530 may obtain the trained reconstruction model by performing an iteration process including one or more iterations. In some embodiments, the reconstruction module 530 may update weight parameters of a preliminary model by performing an iteration process of a backpropagation neural network training procedure, e.g., a stochastic gradient descent backpropagation training technique, to determine the updated values of the weight parameters of the trained reconstruction model. For example, the reconstruction module 530 may backpropagate the error determined for the output of the neural network in order to adjust the parameters of the neural network layers.

In 810, the reconstruction module 530 may output, by an intermediate model, a plurality of output images based on the sample k-space data of one of the plurality of training data sets. For example, the reconstruction module 530 may input the sample k-space data of the one of the plurality of training data sets into the intermediate model. The intermediate model may output the output images based on the sample k-space data. As another example, the reconstruction module 530 may input the sample aliased images corresponding to the sample k-space data of the one of the plurality of training data sets into the intermediate model. The intermediate model may output the output images based on the sample aliased images. In some embodiments, each of the plurality of output images may correspond to one of the plurality of sample images of the one of the plurality of training data sets.

In some embodiments, the intermediate model may include a preliminary model in a first iteration of the one or more iterations of the iteration process or an updated model generated in a previous iteration of the current iteration.

In 820, the reconstruction module 530 may determine a difference between the plurality of output images and the plurality of sample images of the one of the plurality of training data sets. In some embodiments, the reconstruction module 530 may determine a value of a loss function based on the difference.

In 830, the reconstruction module 530 may determine whether a termination condition is satisfied. An exemplary termination condition may be that the value of the loss function in the current iteration is less than a threshold value. Other exemplary termination conditions may include that a maximum number (or count) of iterations has been performed, and/or that a difference between the values of the loss function obtained in a previous iteration and the current iteration (or among the values of the loss function within a certain number or count of successive iterations) is less than a certain threshold. In response to a determination that the termination condition is not satisfied in 830, the process 800 may proceed to 850, and initiate a new iteration by further repeating 810-830 until the termination condition is satisfied. In response to a determination that the termination condition is satisfied in 830, the process 800 may proceed to operation 840, e.g., the iterative process may be terminated and the intermediate model in the current iteration may be determined as the trained reconstruction model, and may be stored and/or output.

In 850, the reconstruction module 530 may update the intermediate model based on the difference between the plurality of output images and the plurality of sample images. For example, the reconstruction module 530 may update the weight parameters in the intermediate model based on the difference between the plurality of output images and the plurality of sample images.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 9:
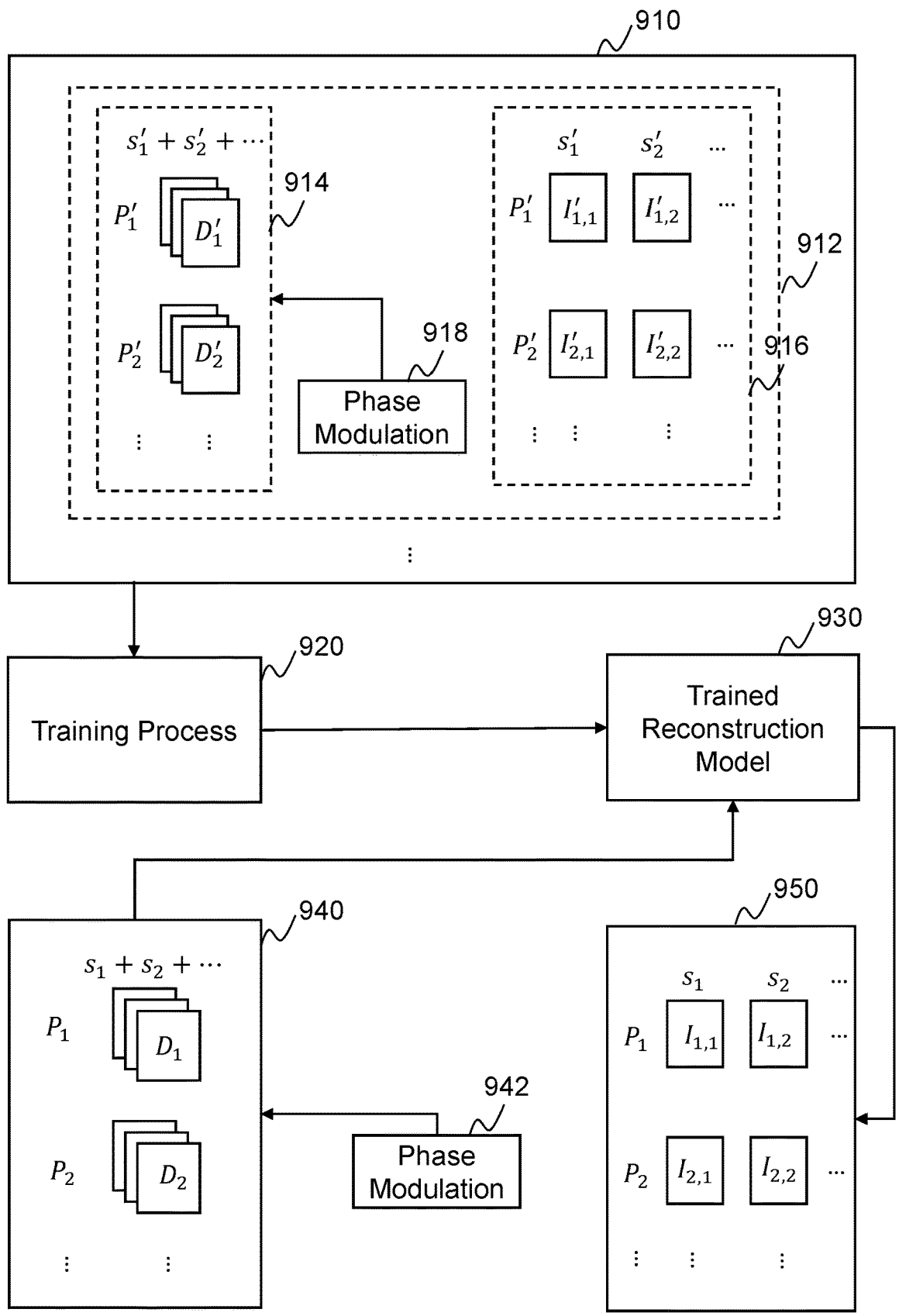
FIG. 9 is a flowchart illustrating an exemplary model training phase and an exemplary model application phase according to some embodiments of the present disclosure.

FIG. 9 is a flowchart illustrating an exemplary model training phase and an exemplary model application phase according to some embodiments of the present disclosure.

Training data 910 (as illustrated in operation 710 of the process 700 in FIG. 7) including a plurality of training data sets (e.g., 912) may be obtained. As shown in FIG. 9, the training data set 912 may include sample k-space data 914 served as training input data and ground truth 916. The sample k-space data 914 may be applied phase modulation 918 (as illustrated in operation 710 of the process 700 in FIG. 7). The sample k-space data 914 may include a plurality of second k-space data sets (e.g., $D_1'$, $D_2'$ ... ) each of which is an aliased k-space data set including k-space from a plurality of sample slices (e.g., $s_1'+s_2'+$ ... ) corresponding to a sample acquisition period (e.g., $P_1'$, $P_2'$ ... ). The ground truth 916 may include a plurality of sample images (e.g., $I_{1,1}'$, $I_{1,2}'$, $I_{2,1}'$, $I_{2,2}'$ ... ) each of which corresponds to a sample slice (e.g., $s_1'$, $s_2'$ ... ) and a sample acquisition period (e.g., $P_1'$, $P_2'$ ... ).

The training data 910 may be used in the training process 920 (as illustrated in operation 720 of the process 700 in FIG. 7 and the process 800 in FIG. 8) to obtain the trained reconstruction model 930.

In application phase of the trained reconstruction model 930, target k-space data 940 (as illustrated in FIGS. 6B-6C, and operation 630 of the process 600 in FIG. 6A) may be input into the trained reconstruction model 930. As shown in FIG. 9, the target k-space data 940 may be applied phase modulation 942 (as illustrated in FIGS. 6B-6C, and operation 620 of the process 600 in FIG. 6A). The target k-space data 940 may include a plurality of first k-space data sets (e.g., $D_1$, $D_2$ ... ) each of which is an aliased k-space data set including k-space from a plurality of target slices (e.g., $s_1+s_2+$ ... ) corresponding to a target acquisition period (e.g., $P_1$, $P_2$ ... ). The output of the trained reconstruction model 930 based on the target k-space data 940 may include a plurality of target unaliased images (e.g., $I_{1,1}$, $I_{1,2}$, $I_{2,1}$, $I_{2,2}$ ... ) each of which corresponds to a target slice (e.g., $s_1$, $s_2$ ... ) and a target acquisition period (e.g., $P_1$, $P_2$ ... ).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 10:
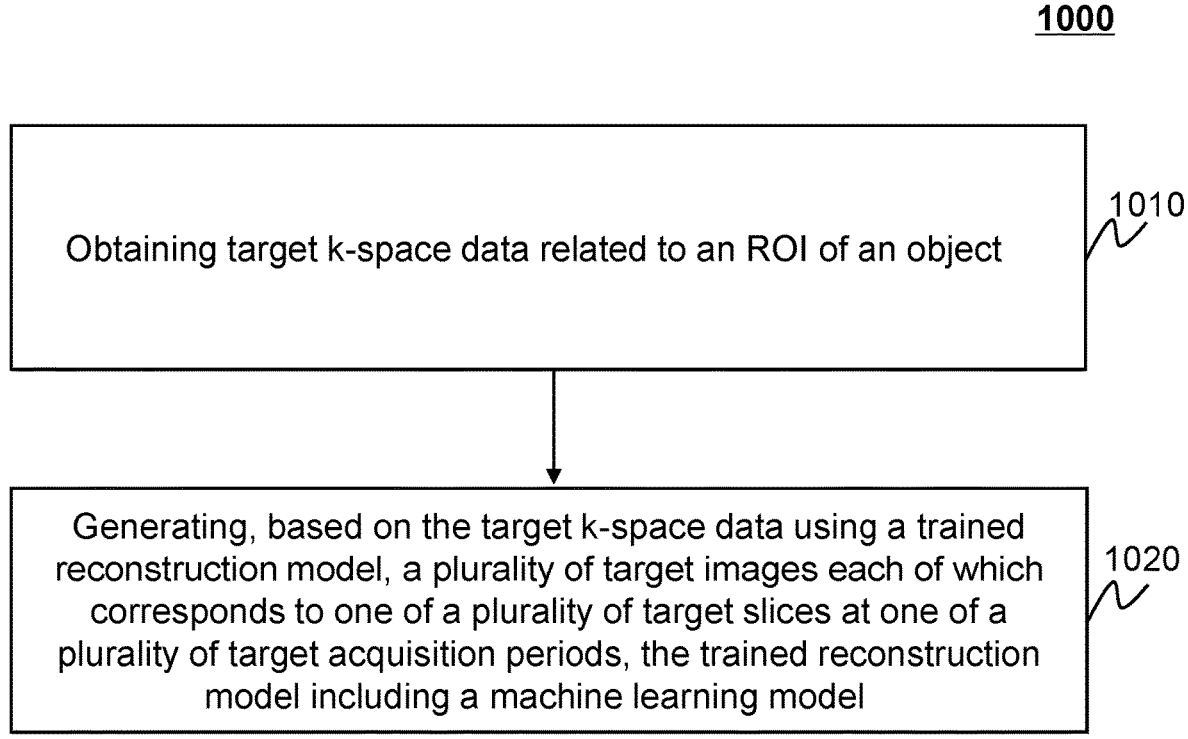
FIG. 10 is a flowchart illustrating an exemplary process for MR imaging according to some embodiments of the present disclosure.

FIG. 10 is a flowchart illustrating an exemplary process for MR imaging according to some embodiments of the present disclosure. In some embodiments, the process 1000 may be implemented in the MRI system 100 illustrated in FIG. 1. For example, the process 1000 may be stored in a storage device (e.g., the storage device 150, or the storage 320 of the processing device 140) as a form of instructions, and can be invoked and/or executed by the processing device 140 (e.g., the processor 310 of the processing device 140, or one or more modules in the processing device 140 illustrated in FIG. 5). The operations of the illustrated process 1000 presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting.

In 1010, the processing device 140 (e.g., the acquisition module 520) may obtain target k-space data related to an ROI of an object.

In some embodiments, the target k-space data may be acquired by scanning, using an MRI device (e.g., the scanner 110), the ROI of the object. In some embodiments, the target k-space data may be acquired by single-slice excitation or multi-slice excitation (e.g., SMS). In some embodiments, the target k-space data may be undersampled or fully sampled.

In some embodiments, the target k-space data may be autocalibration acquisition data including the following features. The target k-space data may be acquired from a plurality of slices of the ROI of the object that are simultaneously excited. The target k-space data may be acquired in a plurality of acquisition periods so that a series of temporal frames each of which corresponds to one of the plurality of slices and one of the plurality of acquisition periods are reconstructed from the target k-space data. The target k-space data may be phase-modulated by applying a transmit phase that varies along the phase encoding direction and/or the temporal dimension (e.g., the plurality of acquisition periods). In some embodiments, the target k-space data may be acquired by performing operations 610 and 620 of the process 600 in FIG. 6A.

In 1020, the processing device 140 (e.g., the reconstruction module 530) may generate, based on the target k-space data using a trained reconstruction model, one or more target images. The trained reconstruction model may be a machine learning model. In some embodiments, the processing device 140 may input the target k-space data into the trained reconstruction model. The trained reconstruction model may output the one or more target images based on the target k-space data.

In some embodiments, the processing device 140 may generate, based on the target k-space data using the trained reconstruction model, a target images corresponding to a target slice of the ROI. In some embodiments, the processing device 140 may generate, based on the target k-space data using a trained reconstruction model, a plurality of target images (temporal frames) each of which corresponds to a same target slice of the ROI and one of a plurality of target acquisition periods. In some embodiments, the processing device 140 may generate, based on the target k-space data using a trained reconstruction model, a plurality of target images each of which corresponds to one of a plurality of target slices of the ROI. In some embodiments, the processing device 140 may generate, based on the target k-space data using a trained reconstruction model, a plurality of target images (temporal frames) each of which corresponds to one of a plurality of target slices of the ROI and one of a plurality of target acquisition periods.

Merely by way of example, the target k-space data may be autocalibration acquisition data described above. The processing device 140 may generate, based on the target k-space data using a trained reconstruction model, a plurality of target images (temporal frames) each of which corresponds to one of a plurality of target slices of the ROI and one of a plurality of target acquisition periods. Details regarding the imaging process in this embodiment may be similar to the description in connection with FIGS. 6A-9 in the present disclosure.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A system for simultaneous multi-slice (SMS) imaging, comprising:
   a magnetic resonance imaging (MRI) device configured to scan a region of interest (ROI) of an object;
   at least one storage device including a set of instructions; and
   at least one processor configured to communicate with the at least one storage device, wherein when executing the set of instructions, the at least one processor is configured to direct the system to perform operations including:
   obtaining target k-space data related to the ROI of the object; and
   generating, based on the target k-space data using a trained reconstruction model, a plurality of target images each of which corresponds to one of a plurality of target slices of the ROI at one of a plurality of target acquisition periods, wherein the generating a plurality of target images comprises:
   generating a plurality of target aliased images based on the target k-space data and generating the plurality of target images based on the plurality of target aliased images using the trained reconstruction model, each of the plurality of target aliased images corresponding to the plurality of target slices and one of the plurality of target acquisition periods; or
   determining a plurality of reference data sets based on the target k-space data and generating the plurality of target images based on the plurality of reference data sets using the trained reconstruction model, each of the plurality of reference data sets corresponding to one of the plurality of target slices and one of the plurality of target acquisition periods, the plurality of reference data sets providing unaliased information for unaliasing of the plurality of target slices in the target k-space data.

2. The system of claim 1, wherein the target k-space data includes a plurality of first k-space data sets each of which is acquired from the plurality of target slices in one of the plurality of target acquisition periods.

3. The system of claim 1, wherein obtaining the target k-space data related to the ROI of the object includes:
   causing the MRI device to apply one or more multiband excitation radio frequency (RF) pulses to the ROI to simultaneously excite, for one or more times, the plurality of target slices of the ROI;
   causing the MRI device to apply phase modulation to at least one of the excited target slices by applying, to each of the at least one of the excited target slices, a transmit phase that varies with a plurality of target acquisition periods and/or a phase encoding direction; and
   acquiring the target k-space data from the plurality of excited target slices of the ROI at the plurality of target acquisition periods.

4. The system of claim 3, wherein the transmit phases applied to two or more of the plurality of target slices are different.

5. The system of claim 1, wherein
   the plurality of target aliased images are generated performing inverse Fourier transform on the target k-space data, and
   the plurality of target images are generated by inputting the plurality of aliased images into the trained reconstruction model.

6. The system of claim 1, wherein the plurality of target images are generated by:
   inputting the target k-space data and the plurality of reference data sets into the trained reconstruction model.

7. The system of claim 1, wherein the trained reconstruction model includes a machine learning model.

8. The system of claim 7, wherein the trained reconstruction model is provided by:
   obtaining a plurality of training data sets, each of the plurality of training data sets including sample k-space data and a plurality of sample unaliased images, wherein
   each of the plurality of sample unaliased images corresponds to one of a plurality of sample slices of a sample and one of a plurality of sample acquisition periods; and
   for each of at least one of the plurality of sample slices, phases of the corresponding sample k-space data vary based on the plurality of sample acquisition periods and/or the phase encoding direction; and
   obtaining the trained reconstruction model by training a preliminary model based on the plurality of training data sets.

9. The system of claim 8, wherein the sample k-space data includes real k-space data that is acquired by simultaneously exciting the plurality of sample slices, the plurality of sample unaliased images being generated based on the sample k-space data.

10. The system of claim 9, wherein the sample k-space data is undersampled.

11. The system of claim 8, wherein the sample k-space data includes synthesized k-space data that is obtained by
    obtaining a plurality of sample k-space data sets by performing Fourier transform on the plurality of sample unaliased images, each of the plurality of sample k-space data sets corresponding to one of the plurality of sample unaliased images; and
    applying phase modulation to the sample k-space data sets so that for each of at least one of the plurality of sample slices, the sample phases of the corresponding sample k-space data sets vary based on the plurality of sample acquisition periods and/or the phase encoding direction; and
    obtaining a plurality of second k-space data sets by combining the sample k-space data sets corresponding to the sample acquisition period, each of the plurality of second k-space data sets corresponding to the plurality of sample slices and one of the plurality of sample acquisition periods, the sample k-space data sets including the plurality of second k-space data sets.

12. The system of claim 11, wherein the synthesized k-space data is obtained further by
    applying an undersampling strategy to the plurality of second k-space data sets or the plurality of sample k-space data sets by replacing a portion of data in the plurality of second k-space data sets or the plurality of sample k-space data sets with zero.

13. The system of claim 8, wherein obtaining the trained reconstruction model by training the preliminary model based on the plurality of training data sets includes:
    for each of at least one of the plurality of training data sets, generating a plurality of sample aliased images by performing inverse Fourier transform on the sample k-space data of the training data set, each of the plurality of sample aliased images corresponding to the plurality of sample slices and one of the plurality of sample acquisition periods; and obtaining the trained reconstruction model by training the preliminary model based on the plurality of sample aliased images of the each of the at least one of the plurality of training data sets.

14. The system of claim 8, wherein obtaining the trained reconstruction model by training the preliminary model based on the plurality of training data sets includes:

obtaining the trained reconstruction model by performing an iteration process including one or more iterations, at least one of the one or more iterations including:

outputting, by an intermediate model, a plurality of output images based on the sample k-space data of one of the plurality of training data sets, the intermediate model including the preliminary model in a first iteration of the one or more iterations of the iteration process or an updated model generated in a previous iteration of the at least one of the one or more iterations, each of the plurality of output images corresponding to one of the plurality of sample unaliased images of the one of the plurality of training data sets; and updating the intermediate model based on a difference between the plurality of output images and the plurality of sample unaliased images of the one of the plurality of training data sets.

15. The system of claim 1, wherein each of the plurality of target acquisition periods corresponds to a physiological motion phase of the ROI; and the plurality of target images form a physiological motion cine of the ROI.

16. The system of claim 15, wherein the ROI of the object includes at least a portion of a heart or a lung.

17. The system of claim 1, wherein the plurality of target images are used for perfusion analysis and indicate a change of a density of a contrast agent in the plurality of target slices over time.

18. A method for simultaneous multi-slice (SMS) imaging implemented on a machine including one or more processors and one or more storage devices, comprising:

obtaining target k-space data related to a region of interest (ROI) of an object; and generating, based on the target k-space data using a trained reconstruction model, a plurality of target images each of which corresponds to one of a plurality of target slices of the ROI at one of a plurality of target acquisition periods, wherein the generating a plurality of target images comprises:

generating a plurality of target aliased images based on on the target k-space data and generating the plurality of target images based on the plurality of target aliased images using the trained reconstruction model, each of the plurality of target aliased images corresponding to the plurality of target slices and one of the plurality of target acquisition periods; or determining a plurality of reference data sets based on the target k-space data and generating the plurality of target images based on plurality of reference data sets using the trained reconstruction model, each of the plurality of reference data sets corresponding to one of the plurality of target slices and one of the plurality of target acquisition periods, the plurality of reference data sets providing unaliased information for unaliasing of the plurality of target slices in the target k-space data.

19. The method of claim 18, wherein the target k-space data including a plurality of first k-space data sets each of which is acquired from the plurality of target slices in one of the plurality of target acquisition periods.

20. A non-transitory computer readable medium, comprising at least one set of instructions, wherein when executed by one or more processors of a computing device, the at least one set of instructions causes the computing device to perform a method, the method comprising:

obtaining target k-space data related to a region of interest (ROI) of an object and generating, based on the target k-space data using a trained reconstruction model, a plurality of target images each of which corresponds to one of a plurality of target slices of the ROI at one of a plurality of target acquisition periods, wherein the generating a plurality of target images comprises:

generating a plurality of target aliased images based on on the target k-space data and generating the plurality of target images based on the plurality of target aliased images using the trained reconstruction model, each of the plurality of target aliased images corresponding to the plurality of target slices and one of the plurality of target acquisition periods; or determining a plurality of reference data sets based on the target k-space data and generating the plurality of target images based on plurality of reference data sets using the trained reconstruction model, each of the plurality of reference data sets corresponding to one of the plurality of target slices and one of the plurality of target acquisition periods, the plurality of reference data sets providing unaliased information for unaliasing of the plurality of target slices in the target k-space data.

* * * * *